(12) United States Patent
Gibbs

(10) Patent No.: US 7,622,273 B2
(45) Date of Patent: Nov. 24, 2009

(54) METHOD FOR CHEMICAL AND ENZYMATIC TREATMENT OF POSTTRANSLATIONALLY MODIFIED PROTEINS BOUND TO A PROTEIN CHIP

(76) Inventor: Bernard F. Gibbs, 6550 Sherbrooke West, Suite 914, Montreal, Quebec (CA) H4B 1N6

( * ) Notice: Subject to any disclaimer, the term of this patent is extended or adjusted under 35 U.S.C. 154(b) by 184 days.

(21) Appl. No.: 11/431,820

(22) Filed: May 11, 2006

(65) Prior Publication Data

US 2006/0269980 A1 Nov. 30, 2006

Related U.S. Application Data

(60) Provisional application No. 60/679,644, filed on May 11, 2005, provisional application No. 60/679,974, filed on May 12, 2005.

(51) Int. Cl.
C12Q 1/37 (2006.01)
(52) U.S. Cl. ...................................................... 435/23
(58) Field of Classification Search .................... 435/4, 435/23

See application file for complete search history.

(56) References Cited

U.S. PATENT DOCUMENTS

| | | | |
|---|---|---|---|
| 5,045,694 | A | 9/1991 | Beavis et al. |
| 5,118,937 | A | 6/1992 | Hillenkamp et al. |
| 5,719,060 | A | 2/1998 | Hutchens et al. |
| 6,225,047 | B1 | 5/2001 | Hutchens et al. |
| 2003/0108949 | A1* | 6/2003 | Bao et al. ...................... 435/7.1 |
| 2003/0124371 | A1* | 7/2003 | Um et al. ...................... 428/522 |
| 2005/0090016 | A1 | 4/2005 | Rich et al. |
| 2006/0269980 | A1* | 11/2006 | Gibbs ........................... 435/23 |
| 2007/0105103 | A1* | 5/2007 | Takeda et al. .................. 435/6 |
| 2007/0117164 | A1* | 5/2007 | Raskov et al. ............... 435/7.23 |

FOREIGN PATENT DOCUMENTS

WO WO 2004/070051 A2 * 8/2004

OTHER PUBLICATIONS

Chow A. et al. Integrating Surface Plasmon Resonance with MS. FASEB J 2004 18(8 Suppl S)C248.*
Aebersold, R. et al., Nature, Mar. 13, 2003, vol. 422, pp. 198-207.
Fenn, J.B. et al., Science, Oct. 6, 1989, vol. 246, No. 4926, pp. 64-71.
Tanaka, K. et al., Rapid Commun. Mass Spectrom., 1988, vol. 2, No. 8, pp. 151-153.
Weinberger, S.R. et al., Encyclopedia of Analytical Chemistry, 2000, vol. 13, pp. 11915-11918, R.A. Meyers, ed., John Wiley & Sons, Chichester, UK.
Petricoin, E.F. et al., The Lancet, Feb. 16, 2002, vol. 359, pp. 572-577.
Petricoin, E.F. et al., Current Opinion in Biotechnology, 2004, vol. 15, pp. 24-30.
Petricoin, E.F. et al., Clinical Chemistry, 2003, vol. 49, No. 4, pp. 533-534.
Ge, Y. et al., 2004, "Salcatonin Qantitation by CHIP-MS Technology", 18th Symposium of the Protein Society, San Diego, CA.
Görg, A., Jul. 2000, "Advances in 2D gel techniques", Proteomics: A Trend Guide, pp. 3-6, Mann, M., Blackstock, W., ed., Elsevier, London, UK.
Link, A.J. et al., Jul. 1999, Nature Biotechnology, vol. 17, pp. 676-682.
Kiernan, U.A. et al., 2003, J Proteome Research, vol. 2, No. 2, pp. 191-197.
Merchant, M. et al., 2000, Electrophoresis, vol. 21, pp. 1164-1177.
Gevaert, K. et al., 2000, Electrophoresis, vol. 21, pp. 1145-1154.
Lin, S. et al., 2001, Proteomics, vol. 1, pp. 1172-1184.
Dare, T.O. et al., 2002, Electrophoresis, vol. 23, pp. 3241-3251.
Caputo, E. et al., 2003, Analytical Biochemistry, vol. 321, pp. 116-124.
Rudd, P. et al., Mar. 23, 2001, Science, vol. 291, pp. 2370-2376.
Kim, Y.J. et al., 1997, Glycoconjugate Journal, vol. 14, pp. 569-576.
Zhen, Y. et al., 2003, Biochemistry, vol. 42, No. 18, pp. 5478-5492.
Cohen, P., Apr. 2002, Nature Reviews, vol. 1, pp. 309-315.
Stein, P.E. et al., Sep. 6, 1990, Nature, vol. 347, pp. 99-102.
Maccoss, M.J. et al., Jun. 11, 2002, PNAS, vol. 99, No. 12, pp. 7900-7905.
Laemmli, U.K., Aug. 15, 1970, Nature (Lond.), vol. 227, pp. 680-685.
Washburn, M.P. et al., Mar. 2001, Nature Biotechnology, vol. 19, pp. 242-247.
Yates, J.R. III, 2004, Annu. Rev. Biophys. Biomol. Struct., vol. 33, pp. 297-316.
Karas, M. et al., 1988, Anal. Chem., vol. 60, pp. 2299-2301.
Bradford, M.M., 1976, Analytical Biochemistry, vol. 72, pp. 248-254.

(Continued)

*Primary Examiner*—Ralph Gitomer
(74) *Attorney, Agent, or Firm*—Goudreau Gage Dubuc

(57) ABSTRACT

The invention provides a simple and quick protocol for chemical treatment, enzymatic or chemical digestion, and subsequent identification of proteins or polypeptides on a protein chip such as protein chip arrays. The chemical treatment includes denaturation, reduction and alkylation while the enzymatic digestion includes deglycosylation, dephosphorylation, and digestion by various proteases. The proteins or polypeptides can also be digested by using various chemicals that are known to induce proteolysis. All reactions are carried out sequentially on chip. Subsequent peptide mass fingerprinting or product ion searches allow the identification of specific peptides, which can be correlated to proteins. The methods of the present invention can be used to analyze biological samples such as urine and plasma and to identify biomarkers in diseased states. The methods of the present invention allow complete on chip treatment, which can be used for rapid protein identification and structural characterization of heavily posttranslationally modified proteins.

19 Claims, 9 Drawing Sheets

OTHER PUBLICATIONS

Duffin, K.L. et al., Jul. 1, 1992, Anal. Chem., vol. 64, No. 13, pp. 1440-1448.

Spiro, R.G. et al., Sep. 25, 1974, The Journal of Biological Chemistry, vol. 249, No. 18, pp. 5704-5717.

Nilsson, B. et al., Jun. 10, 1979, The Journal of Biological Chemistry, vol. 254, No. 11, pp. 4545-4553.

Ge, Y. et al., May 2005, "Complete Chemical and Enzymatic treatment of Posttranslationally Modified Proteins on chips", 52nd Conference ASMS, San Antonio, TX.

Ge, Y. et al., Jun. 1, 2005, Analytical Chemistry, vol. 77, No. 11, pp. 3644-3650.

* cited by examiner

SEQUENCE LISTING

<160> NUMBER OF SEQ ID NOS: 5

<210> SEQ ID NO 1
<211> LENGTH: 621
<212> TYPE: PRT
<213> ORGANISM: Homo sapiens (EGFRED)

<400> SEQUENCE: 1

Leu Glu Glu Lys Lys Val Cys Gln Gly Thr Ser Asn Lys Leu Thr Gln
1               5                   10                  15

```
Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
        50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
            115                 120                 125

Asn Pro Ala Leu Cys Asn Val Glu Ser Ile Gln Trp Arg Asp Ile Val
130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
            165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
            195                 200                 205

His Asn Gln Cys Ala Ala Gly Cys Thr Gly Pro Arg Glu Ser Asp Cys
            210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
            245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
            275                 280                 285

Ala Asp Ser Tyr Glu Met Glu Glu Asp Gly Val Arg Lys Cys Lys Lys
            290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
            325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
            405                 410                 415

Val Ser Leu Asn Ile Thr Ser Leu Gly Leu Arg Ser Leu Lys Glu Ile
            420                 425                 430
```

```
Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser
    610                 615                 620

<210> SEQ ID NO 2
<211> LENGTH: 341
<212> TYPE: PRT
<213> ORGANISM: Bos taurus (Fetuin)

<400> SEQUENCE: 2

Ile Pro Leu Asp Pro Val Ala Gly Tyr Lys Glu Pro Ala Cys Asp Asp
1               5                   10                  15

Pro Asp Thr Glu Gln Ala Ala Leu Ala Ala Val Asp Tyr Ile Asn Lys
            20                  25                  30

His Leu Pro Arg Gly Tyr Lys His Thr Leu Asn Gln Ile Asp Ser Val
        35                  40                  45

Lys Val Trp Pro Arg Arg Pro Thr Gly Glu Val Tyr Asp Ile Glu Ile
    50                  55                  60

Asp Thr Leu Glu Thr Thr Cys His Val Leu Asp Pro Thr Pro Leu Ala
65                  70                  75                  80

Asn Cys Ser Val Arg Gln Gln Thr Gln His Ala Val Glu Gly Asp Cys
                85                  90                  95

Asp Ile His Val Leu Lys Gln Asp Gly Gln Phe Ser Val Leu Phe Thr
            100                 105                 110

Lys Cys Asp Ser Ser Pro Asp Ser Ala Glu Asp Val Arg Lys Leu Cys
        115                 120                 125

Pro Asp Cys Pro Leu Leu Ala Pro Leu Asn Asp Ser Arg Val Val His
    130                 135                 140

Ala Val Glu Val Ala Leu Ala Thr Phe Asn Ala Glu Ser Asn Gly Ser
145                 150                 155                 160

Tyr Leu Gln Leu Val Glu Ile Ser Arg Ala Gln Phe Val Pro Leu Pro
                165                 170                 175

Val Ser Val Ser Val Glu Phe Ala Val Ala Ala Thr Asp Cys Ile Ala
            180                 185                 190
```

```
Lys Glu Val Val Asp Pro Thr Lys Cys Asn Leu Leu Ala Glu Lys Gln
            195                 200                 205

Tyr Gly Phe Cys Lys Gly Ser Val Ile Gln Lys Ala Leu Gly Gly Glu
        210                 215                 220

Asp Val Arg Val Thr Cys Thr Leu Phe Gln Thr Gln Pro Val Ile Pro
225                 230                 235                 240

Gln Pro Gln Pro Asp Gly Ala Glu Ala Glu Ala Pro Ser Ala Val Pro
                245                 250                 255

Asp Ala Ala Gly Pro Thr Pro Ser Ala Ala Gly Pro Pro Val Ala Ser
                260                 265                 270

Val Val Val Gly Pro Ser Val Ala Val Pro Leu Pro Leu His Arg
            275                 280                 285

Ala His Tyr Asp Leu Arg His Thr Phe Ser Gly Val Ala Ser Val Glu
        290                 295                 300

Ser Ser Ser Gly Glu Ala Phe His Val Gly Lys Thr Pro Ile Val Gly
305                 310                 315                 320

Gln Pro Ser Ile Pro Gly Gly Pro Val Arg Leu Cys Pro Gly Arg Ile
                325                 330                 335

Arg Tyr Phe Lys Ile
            340

<210> SEQ ID NO 3
<211> LENGTH: 385
<212> TYPE: PRT
<213> ORGANISM: Gallus gallus (Ovalbumin)

<400> SEQUENCE: 3

Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
            20                  25                  30

Ala Ile Met Ser Ala Leu Ala Met Val Tyr Leu Gly Ala Lys Asp Ser
        35                  40                  45

Thr Arg Thr Gln Ile Asn Lys Val Val Arg Phe Asp Lys Leu Pro Gly
    50                  55                  60

Phe Gly Asp Ser Ile Glu Ala Gln Cys Gly Thr Ser Val Asn Val His
65                  70                  75                  80

Ser Ser Leu Arg Asp Ile Leu Asn Gln Ile Thr Lys Pro Asn Asp Val
                85                  90                  95

Tyr Ser Phe Ser Leu Ala Ser Arg Leu Tyr Ala Glu Glu Arg Tyr Pro
            100                 105                 110

Ile Leu Pro Glu Tyr Leu Gln Cys Val Lys Glu Leu Tyr Arg Gly Gly
        115                 120                 125

Leu Glu Pro Ile Asn Phe Gln Thr Ala Ala Asp Gln Ala Arg Glu Leu
    130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
                165                 170                 175

Ala Ile Val Phe Lys Gly Leu Trp Glu Lys Ala Phe Lys Asp Glu Asp
            180                 185                 190

Thr Gln Ala Met Pro Phe Arg Val Thr Glu Gln Glu Ser Lys Pro Val
        195                 200                 205

Gln Met Met Tyr Gln Ile Gly Leu Phe Arg Val Ala Ser Met Ala Ser
```

-continued

```
                210                 215                 220
Glu Lys Met Lys Ile Leu Glu Leu Pro Phe Ala Ser Gly Thr Met Ser
225                 230                 235                 240

Met Leu Val Leu Leu Pro Asp Glu Val Ser Gly Leu Glu Gln Leu Glu
                245                 250                 255

Ser Ile Ile Asn Phe Glu Lys Leu Thr Glu Trp Thr Ser Ser Asn Val
                260                 265                 270

Met Glu Glu Arg Lys Ile Lys Val Tyr Leu Pro Arg Met Lys Met Glu
                275                 280                 285

Glu Lys Tyr Asn Leu Thr Ser Val Leu Met Ala Met Gly Ile Thr Asp
                290                 295                 300

Val Phe Ser Ser Ala Asn Leu Ser Gly Ile Ser Ser Ala Glu Ser
305                 310                 315                 320

Leu Lys Ile Ser Gln Ala Val His Ala Ala His Ala Glu Ile Asn Glu
                325                 330                 335

Ala Gly Arg Glu Val Val Gly Ser Ala Glu Ala Gly Val Asp Ala Ala
                340                 345                 350

Ser Val Ser Glu Glu Phe Arg Ala Asp His Pro Phe Leu Phe Cys Ile
                355                 360                 365

Lys His Ile Ala Thr Asn Ala Val Leu Phe Phe Gly Arg Cys Val Ser
                370                 375                 380

Pro
385

<210> SEQ ID NO 4
<211> LENGTH: 583
<212> TYPE: PRT
<213> ORGANISM: Rattus norvegicus (RUA)

<400> SEQUENCE: 4

Ala His Lys Ser Glu Ile Ala His Arg Phe Lys Asp Leu Gly Glu Gln
1               5                   10                  15

His Phe Lys Gly Leu Val Leu Ile Ala Phe Ser Gln Tyr Leu Gln Lys
                20                  25                  30

Cys Pro Tyr Glu Glu His Ile Lys Leu Val Gln Glu Val Thr Asp Phe
            35                  40                  45

Ala Lys Thr Cys Val Ala Asp Glu Asn Ala Glu Asn Cys Asp Lys Ser
        50                  55                  60

Ile His Thr Leu Phe Gly Asp Lys Leu Cys Ala Ile Pro Lys Leu Arg
65                  70                  75                  80

Asp Asn Tyr Gly Glu Leu Ala Asp Cys Cys Ala Lys Gln Glu Pro Glu
                85                  90                  95

Arg Asn Glu Cys Phe Leu Gln His Lys Asp Asp Asn Pro Asn Leu Pro
            100                 105                 110

Pro Phe Gln Arg Pro Glu Ala Glu Ala Met Cys Thr Ser Phe Gln Glu
        115                 120                 125

Asn Pro Thr Ser Phe Leu Gly His Tyr Leu His Glu Val Ala Arg Arg
130                 135                 140

His Pro Tyr Phe Tyr Ala Pro Glu Leu Leu Tyr Tyr Ala Glu Lys Tyr
145                 150                 155                 160

Asn Glu Val Leu Thr Gln Cys Cys Thr Glu Ser Asp Lys Ala Ala Cys
                165                 170                 175

Leu Thr Pro Lys Leu Asp Ala Val Lys Glu Lys Ala Leu Val Ala Ala
            180                 185                 190
```

```
Val Arg Gln Arg Met Lys Cys Ser Ser Met Gln Arg Phe Gly Glu Arg
        195                 200                 205

Ala Phe Lys Ala Trp Ala Val Ala Arg Met Ser Gln Arg Phe Pro Asn
    210                 215                 220

Ala Glu Phe Ala Glu Ile Thr Lys Leu Ala Thr Asp Val Thr Lys Ile
225                 230                 235                 240

Asn Lys Glu Cys Cys His Gly Asp Leu Leu Glu Cys Ala Asp Asp Arg
                245                 250                 255

Ala Glu Leu Ala Lys Tyr Met Cys Glu Asn Gln Ala Thr Ile Ser Ser
            260                 265                 270

Lys Leu Gln Ala Cys Cys Asp Lys Pro Val Leu Gln Lys Ser Gln Cys
        275                 280                 285

Leu Ala Glu Thr Glu His Asp Asn Ile Pro Ala Asp Leu Pro Ser Ile
    290                 295                 300

Ala Ala Asp Phe Val Glu Asp Lys Glu Val Cys Lys Asn Tyr Ala Glu
305                 310                 315                 320

Ala Lys Asp Val Phe Leu Gly Thr Phe Leu Tyr Glu Tyr Ser Arg Arg
                325                 330                 335

His Pro Asp Tyr Ser Val Ser Leu Leu Leu Arg Leu Ala Lys Lys Tyr
            340                 345                 350

Glu Ala Thr Leu Glu Lys Cys Cys Ala Glu Gly Asp Pro Pro Ala Cys
        355                 360                 365

Tyr Gly Thr Val Leu Ala Glu Phe Gln Pro Leu Val Glu Glu Pro Lys
    370                 375                 380

Asn Leu Val Lys Thr Asn Cys Glu Leu Tyr Glu Lys Leu Gly Glu Tyr
385                 390                 395                 400

Gly Phe Gln Asn Ala Val Leu Val Arg Tyr Thr Gln Lys Ala Pro Gln
                405                 410                 415

Val Ser Thr Pro Thr Leu Val Glu Ala Ala Arg Asn Leu Gly Arg Val
            420                 425                 430

Gly Thr Lys Cys Cys Thr Leu Pro Glu Ala Gln Arg Leu Pro Cys Val
        435                 440                 445

Glu Asp Tyr Leu Ser Ala Ile Leu Asn Arg Leu Cys Val Leu His Glu
    450                 455                 460

Lys Thr Pro Val Ser Glu Lys Val Thr Lys Cys Cys Ser Gly Ser Leu
465                 470                 475                 480

Val Glu Arg Arg Pro Cys Phe Ser Ala Leu Thr Val Asp Glu Thr Tyr
                485                 490                 495

Val Pro Lys Glu Phe Lys Ala Glu Thr Phe Thr Phe His Ser Asp Ile
            500                 505                 510

Cys Thr Leu Pro Asp Lys Glu Lys Gln Ile Lys Lys Gln Thr Ala Leu
        515                 520                 525

Ala Glu Leu Val Lys His Lys Pro Lys Ala Thr Glu Asp Gln Leu Lys
    530                 535                 540

Thr Val Met Gly Asp Phe Ala Gln Phe Val Asp Lys Cys Cys Lys Ala
545                 550                 555                 560

Ala Asp Lys Asp Asn Cys Phe Ala Thr Glu Gly Pro Asn Leu Val Ala
                565                 570                 575

Arg Ser Lys Glu Ala Leu Ala
            580

<210> SEQ ID NO 5
<211> LENGTH: 162
<212> TYPE: PRT
```

```
<213> ORGANISM: Rattus norvegicus (AUG)

<400> SEQUENCE: 5

Glu Glu Ala Ser Ser Thr Arg Gly Asn Leu Asp Val Ala Lys Leu Asn
1               5                   10                  15

Gly Asp Trp Phe Ser Ile Val Val Ala Ser Asn Lys Arg Glu Lys Ile
            20                  25                  30

Glu Glu Asn Gly Ser Met Arg Val Phe Met Gln His Ile Asp Val Leu
            35                  40                  45

Glu Asn Ser Leu Gly Phe Lys Phe Arg Ile Lys Glu Asn Gly Glu Cys
        50                  55                  60

Arg Glu Leu Tyr Leu Val Ala Tyr Lys Thr Pro Glu Asp Gly Glu Tyr
65                  70                  75                  80

Phe Val Glu Tyr Asp Gly Gly Asn Thr Phe Thr Ile Leu Lys Thr Asp
                85                  90                  95

Tyr Asp Arg Tyr Val Met Phe His Leu Ile Asn Phe Lys Asn Gly Glu
            100                 105                 110

Thr Phe Gln Leu Met Val Leu Tyr Gly Arg Thr Lys Asp Leu Ser Ser
            115                 120                 125

Asp Ile Lys Glu Lys Phe Ala Lys Leu Cys Glu Ala His Gly Ile Thr
        130                 135                 140

Arg Asp Asn Ile Ile Asp Leu Thr Lys Thr Asp Arg Cys Leu Gln Ala
145                 150                 155                 160

Arg Gly
```

METHOD FOR CHEMICAL AND ENZYMATIC TREATMENT OF POSTTRANSLATIONALLY MODIFIED PROTEINS BOUND TO A PROTEIN CHIP

CROSS REFERENCE TO RELATED APPLICATIONS

This application claims priority on U.S. provisional application No. 60/679,644, filed on May 11, 2005 and on U.S. provisional application 60/679,974 filed on May 12, 2005. All documents above are herein incorporated by reference.

FIELD OF THE INVENTION

The present invention relates to proteomics. More particularly, the present invention relates to protein chip arrays. More specifically, the present invention is concerned with methods of chemical and enzymatic treatment of proteins on protein chips and kits therefor. More particularly, the invention relates to chemical and enzymatic treatment of posttranslationally modified proteins on protein chip arrays.

BACKGROUND OF THE INVENTION

Many advances in proteomics have been driven by the development of mass spectrometric-based technologies and tools[1]. Although mass spectrometry (MS) was invented in the early 1900s for the detection of small molecules, a quantum leap was achieved in the late 1980s when Fenn and Tanaka showed independently that large biomolecules (proteins, deoxy ribonucleic acid (DNA), etc) can be detected and quantitated accurately by MS. Fenn's technique called Electro Spray Ionization (ESI) nebulizes a protonated liquid into a fine spray using a high voltage prior to MS detection[2]. Tanaka's method called Matrix Assisted Laser Desorption Ionization (MALDI) utilizes a high energy absorbing molecule to desorb intact proteins on a solid inert surface[3]. A flavor of this latter technique, called Surface Enhanced Laser Desorption Ionization (SELDI) permits the immobilization of molecules on different active surfaces. SELDI is described in U.S. Pat. No. 5,719,060[4], U.S. Pat. No. 6,225,047[5], and in Weinberger et al., 2000[6].

A number of reports have appeared over the past few years regarding proteomic profiling with SELDI-TOF technology, in combination with artificial intelligence[7]. Reported sensitivities and specificities with the technique for ovarian, prostate, and breast cancer diagnoses are better than those obtained with current serologic cancer biomarkers[8]. Also, the technique is reported to detect early as well as late stage disease with similar efficiency, thus offering a potentially powerful new cancer screening tool[9].

Extremely better specificies and sensitivities are obtained if the SELDI chipholder is analysed by a high resolution mass spectrometer (e.g. ABI/Sciex QSTAR ms)[10]. A Tandem MS interface, model PCI-1000 is available from Ciphergen Biosystens for such purposes.

The combination of techniques such as polyacrylamide gel electrophoresis (PAGE)[7,8], reverse phase high performance liquid chromatography (RP-HPLC)[9-11], affinity capture[12,13] and protein chips[14] with mass spectrometry (MS) has provided a series of important tools for the investigation of numerous facets of proteomics. The identification and characterization of the chemical features of proteins are essential prerequisites for understanding the dynamics and connectivity of their interactions as well as the diversity of their biological functions in living organisms. As a common method, peptide mass fingerprinting (PMF) identifies proteins by comparing the peptide mass fingerprint obtained from mass spectrometry analysis of enzymatic (or chemical) digestions to mass profiles generated by in-silico digestion of proteins[15]. This approach requires relatively purified target protein and is often used with protein fractionation techniques. Prior to enzymatic or chemical digestion, proteins are denatured, reduced and alkylated. Digestion is generally performed overnight to ensure complete cleavage. Structural characterization of proteins becomes all the more difficult if one considers that the vast majority of proteins contain disulfide bridges, phosphorylation, glycosylation sites or a combination of the above. Another less popular but more powerful method than PMF is the analysis of ms/ms product ion spectra to determine the peptide backbone fragmentation.

Thus, to study biological systems at the protein level, efforts have been directed at improvements in instrumentation and the development of novel technologies.

Protein chip array technology is based on two powerful techniques: chromatography and mass spectroscopy. It consists of selective protein extraction, retention and enrichment of proteins on chromatographic chip surfaces and their subsequent analysis by mass spectroscopy. The protein chip array surfaces function as a solid phase extraction media that support isolation and clean up of analytes prior to mass spectroscopic investigation.

By comparing samples between control and experimental groups or between healthy and diseased individuals, in one use of the technology, protein chip array profiling allows the rapid creation of phenotypic fingerprints and the identification of biomarkers of particular metabolic or disease states.

Thus, together with the growth of this technology comes the need for protein chemistry techniques that are applicable to protein chips. Three groups have reported a single on-chip reaction prior to MS analysis. Pentafluoropropionic acid and trifluoroacetic acid (TFA) were used to perform limited acid hydrolysis of proteins using a vapor-phase hydrolysis procedure[16]. The method was proposed to generate peptide ladders indicating primary sequences. However, side reactions, such as oxidation of methionine residues and deamidation of asparagine or glutamine, were systematically observed[16]. A second group reported a procedure for the identification of parvalbumin alpha (PVA) using on-chip enzymatic proteolysis[17]. Four peptides were identified after a 2-hour digestion and nine peptides were identified after 18 hours. PVA is an 11.85 kilodalton (kDa) linear N-terminus acetylated polypeptide, which is not representative of most of the proteins in existing proteomes as it lacks complex modifications such as disulfide bridges, phosphorylated or glycosylated moieties. Finally, an on-chip tryptic digestion method has been applied to recombinant prolactin-inducible protein (PIP). This purified 16.57 kDa protein has two disulfide bridges and one N-glycosylation site[18].

In all the above examples, most chemical and enzymatic steps were carried out in solution. Relatively simple proteins were tested, and in all cases, a single on-chip step of treatment was performed. On-chip protein denaturation, reduction, alkylation, deglycosylation and dephosphorylation using protein chips have not been previously reported. In addition, previous reports have generally been based on rather simple proteins.

Thus, there remains a need for improved methods allowing structural characterization of proteins.

There further remains a need for methods of protein identification, which reduce sample loss, enable rapid and sensitive detection and identification of proteins with minimal sample manipulation.

There also remains a need for simple methods allowing complete on-chip chemistry (including enzymatic treatment) and characterization of proteins.

The present invention seeks to meet these needs and other needs.

The present description refers to a number of documents, the content of which is herein incorporated by reference in their entirety.

SUMMARY OF THE INVENTION

Although solid phase chemistry (e.g. Edman degradation) has been routinely performed on solid support for years, it is difficult to imagine complex biochemical reactions on solid surfaces partly because the enzymes must retain their activities throughout the process, and also because of limited bioavailability. For example, in enzymatic digestion, the reactants seem unlikely to interact effectively to cleave highly complex proteins. It is analogous to putting liquid in sand as a first step, followed by an addition of different liquids and expect proper mixing. When a protein is denatured, it is in its most relaxed state and more prone to interact with other species. A solid small surface is not a predictable environment for that interaction. Reactions in solution have been carried out for centuries and are fully understood (accessibility to water, configuration of the protein in solution, etc.). However, biochemical reactions on solid surfaces have been very poorly exploited because of their complexity and also because they seem not likely to occur. For example, the environment of the protein on a chip is very different from that in solution. The water environment is one critical difference between proteins on a chip as compared to that in solution. The relatively dry state of a protein on a chip suggests that enzymatic digestion is likely not to occur on a chip.

The rapid growth of proteomics and more particularly protein array technology urged the development of simpler, more sensitive methodologies. Microfabricated devices are becoming increasingly popular for the analysis of biomolecules (DNA, ribonucleic acid (RNA), proteins, peptides, etc.) for a number of reasons. These devices come in two varieties, the array format and microfluidic devices. They offer the potential to automate biological sample processing (reduction, alkylation, chemical and enzymatic digestion, desalting, etc.) reduce costs and increase throughput. In addition, they are designed with minimal quantities of sample to be used. When only tiny amounts of sample are available, macroscale techniques become ineffective due to sample losses.

Researchers around the world have attached great importance to protein chip technology because it could in theory simultaneously analyze information of many biomolecules in one reaction. However, the development and applications of this technology is still limited by its complexity.

The present invention surprisingly demonstrates that several complex enzymatic and chemical reactions can indeed be performed directly on protein chip surfaces in a sequential fashion.

Thus, the present invention relates to the use of protein chip methods and kits for performing various enzymatic as well as other biological and chemical reactions. This approach employs chips with different surface physicochemical properties enabling the selective capture and retention of proteins or peptides from biological samples.

In one aspect, the present invention relates to protein chemistry procedures that can be performed directly on-chip using small volumes (in the µl rangem e.g. 0.5-5.0 µl) of the biological sample of interest, reagents and washing solutions, as well as relatively short reaction time for both chemical and enzymatic treatments prior to MS analysis.

More specifically, the present invention is concerned with a quick, simple and sensitive method allowing two or more, and up to all chemical reactions to be performed on-chip as well as subsequent enzymatic deglycosylation, dephosphorylation and proteolysis in a sequential fashion. The methods of the present invention provide a rapid and simple alternative to in-gel or in-solution methods.

Thus, the present invention is concerned with novel experimental methods to analyze peptide/proteins by protein chip array technology. These methods enable the rapid deglycosylation, dephosphorylation, digestion and identification of low amounts (in the picomolar range) of complex proteins. Because all steps may be performed directly on-chip, the method of the present invention is easily amenable to automation. Consequently, the method of the present invention may be developed for low-throughput, high-throughput, or ultra-high throughput analysis formats.

In one aspect, the method of the present invention generally comprises a number of the following steps:

a) conditioning of the spots of the protein chip array with conditioning buffer;

b) loading of the biological sample on the protein chip; after binding, excess sample is removed and each spot is washed with appropriate buffer;

c) denaturing the protein sample;

d) reducing the protein sample;

e) alkylating the protein sample;

f) deglycosylating and/or dephosphorylating the sample;

g) chemical or enzymatic digestion (hydrolysis of peptide bonds) for PMF;

h) performing MS analysis (drying of the sample, matrix (energy absorbing molecule-EAM) addition and data collection); and i) database mining and identification of proteins.

In accordance with the present invention only some steps of the above general method may be performed depending on the type of information that is sought and the type of protein sample and protein chip that is used. For example, if information is only sought on the phosphorylation status of the protein, then, the deglycosylation and chemical/enzymatic digestion steps may not be performed. Alternatively, if only the glycosylation level of a protein needs to be studied then, the dephosphorylation and chemical/enzymatic digestion steps would not be performed. On the other hand if one is working with relatively simple proteins or peptides, then the dephosphorylation and deglycosylation step may not be required. In addition, the particular chip used may not require a conditioning step or may come already conditioned. Thus, depending on the particular experimental requirements, a person skilled in the art would choose which of the above steps are to be performed and adapt the method accordingly.

Thus, in one embodiment, the method of the present invention comprises a conditioning step (if required), a biological sample loading step, a denaturing step, a reducing step, an alkylating step, a deglycosylation step, an enzymatic or chemical digestion step and an MS analysis step.

In another embodiment, the method of the present invention comprises a conditioning step (if required), a biological sample loading step, a denaturing step, a reducing step, an alkylating step, a dephosphorylation step, an enzymatic or chemical digestion step and an MS analysis step.

In a further embodiment, the method of the present invention comprises a conditioning step (if required), a biological sample loading step, a denaturing step, a reducing step, an alkylating step, a deglycosylation step, a dephosphorylation step and an MS analysis step.

In yet another embodiment, the method of the present invention comprises a conditioning step (if required), a biological sample loading step, a denaturing step, a reducing step, an alkylating step, a deglycosylation and/or dephosphorylation step and a MS analysis step.

In another additional embodiment, the method of the present invention comprises a conditioning step (if required), a biological sample loading step, a denaturing step, a reducing step, an enzymatic or chemical digestion step for PMF (peptide mass fingerprinting) and an ms/ms ion search or sequence query in the MS analysis step.

In yet a further embodiment, the enzymatic digestion step is replaced by a chemical digestion step (e.g. acid hydrolysis step).

In one embodiment, the deglycosylation step is performed prior to the dephosphorylation step. In another embodiment the dephosphorylation step is performed before the deglycosylation step.

In another embodiment, the present invention relates to kits for performing direct on chip protein or peptide analysis in accordance with the present invention. Such kits may comprise one or more containers containing reagents (e.g. reducing reagents, denaturing, deglycosylating reagents, dephosphorylating reagents, alkylating reagents and/or reagents for chemically or enzymatically cleaving the peptide or protein) together with instructions for performing a number of steps required for on-chip protein/peptide analysis together. The kits may further comprise one or more chips for performing the analysis. Alternatively, the chip and/or some of the reagents (e.g. reducing reagents, denaturing, deglycosylating reagents, dephosphorylating reagents, alkylating reagents and/or reagents for chemically or enzymatically cleaving the peptide or protein) may be provided separately from the kit.

Thus, in one embodiment, the present invention relates to a kit for analysing a protein or peptide directly on-chip comprising container means comprising at least 2 of the following reagents; a) denaturing reagents; b) reducing reagents; c) alkylating reagents; d) deglycosylating reagents; e) dephosphorylating reagents; and f) reagents for chemically or enzymatically cleaving said protein or peptide, together with instruction for performing direct on-chip protein or peptide analysis.

In one particular embodiment, the kit of the present invention comprises at least 3, at least 4, at least 5 or at least 6 of the following reagents: a) denaturing reagents; b) reducing reagents; c) alkylating reagents; d) deglycosylating reagents; e) dephosphorylating reagents; and f) reagents for chemically or enzymatically cleaving said protein or peptide, together with instruction for performing direct on-chip protein or peptide analysis.

In a further embodiment, the above kits are provided with one or more chips an, optionally, conditioning reagents for the chips. The chips may be of the same type or alternatively they may be of different types. Any suitable types of chips may be used in accordance with the present invention. The kits may be customized in accordance with the specific requirements of the protein or peptide analyses that are to be performed. Of course all reagents provided with the kits in accordance with the present invention may be stored in the same containers means (e.g. when one or more of the above method steps can be performed at the same time) or in separate container means, depending on the specific requirements of the kit.

For example, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample (protein or peptide), containers which contain enzymes or chemical reagents, containers which contain wash reagents, etc.

When performing protein characterization spectrometry analysis, it is often desirable to cleave proteins directly on the chip into smaller fragments (peptides) using cleaving reagents for either chemical or enzymatic cleavage. As well known in the art, the digestion of proteins into small fragments provides a mass fingerprint that can be used to determine the protein identity and other characteristics such as posttranslational chemical modifications to specific residues. Thus, the specific fragments that result from digestion can be used as a fingerprint for protein identification by a technique known as peptide mass fingerprinting (PMF). Also, proteolytic fragmentation is useful for high molecular weight proteins because smaller fragments are often more easily measured and resolved by mass spectrometry and chemical modifications can be isolated to specific peptide regions of a protein.

Thus, in one aspect of the present invention, the enzymatic and/or chemical cleavage of proteins/peptides present in a sample is performed directly on the chip. Subsequent MS analysis is performed in order to obtain a fingerprint of the proteins/peptides or a product ion spectrum to determine their identity.

In accordance with the present invention, several enzymes having different specificity (i.e. cleaving after specific amino acid residues) can be used for PMF or product ion spectra for subsequent identification of protein fragments by MS analysis. Proteases, such as trypsin, that cleave proteins into a discrete number of predictable fragments are particularly useful. Other non-limiting examples of enzymes that may be used for direct on-chip digestion include, V8-protease, Arg-C proteinase, Asp-N endopeptidase, Glu-C endoproteinase, Lys-C endopeptidase, chymotrypsin, pepsin, aminopeptidase M, carboxypeptidase-A, carboxypeptidase-B, carboxypeptidase-Y, caspases 1-10, clostropain (Clostridiopeptidase B), elastase, enterokinase, factor Xa, glutamyl endopeptidase, granzyme B, papain, proline-endopeptidase, pronase, proteinase K, staphylococcal peptidase 1, thermolysin, and thrombin.

As an alternative or complementary approach to enzymatic cleavage for PMF, direct, on-chip chemical cleavage may also be used in. accordance with the present invention. Non-limiting examples of compatible reagents that can be used include 2-(2-nitrophenylsulfenyl)-3-bromo-methylindolenine (BNPS-Skatole), Cyanogen Bromide (CNBr), CNBr/heptafluorobutyric acid, Dimethylsulfoxide (DMSO)/HCl and DMSO/Hydrogen bromide (HBr), DMSO/HCl and CNBr, formic acid, hydroxylamine, iodosobenzoic acid, N-bromosuccinimide, N-chlorosuccinimide, 2-nitro-5-thiocyanobenzoic acid (NTCB) and tribromocresol.

Of course the choice of the particular enzyme or mixture of enzymes to be used will depend on the type of sample (e.g. whether large proteins or peptides are analyzed, the structural properties of the protein(s) to be analyzed, etc) and on the information that is sought. Similarly, the particular choice of chemical reagent used will depend on these factors. In addition, the digestion parameters (reaction time, amount of enzyme(s), digestion buffer to be used, etc.) should be adapted to suit the concentration and type of sample that is hydrolyzed and the particular protein chip surface that is used, as well known in the art. Of course mixtures of enzymes, mixtures of chemical reagents and combination of enzymes and chemical reagents may be used in accordance with the present invention. Provided that they are compatible to one another, the particular enzyme and chemical treatments used may be performed directly and simultaneously on the protein chip surface. Alternatively one or more enzymatic treatment(s) or one or more chemical treatments may be performed directly on-chip in a sequential fashion depending on the specific experimental requirements. Of course the treatments used need to be chosen or adapted so as to enable MS.

The protein chip surface to be used in accordance with the methods of the present invention depends on the particular physicochemical properties of the protein/peptide sample to be analyzed. Several chip surface arrays are commercially available (e.g. Ciphergen Biosystems, Palo Alto, Calif., USA). They are generally derivatized with classic chromatographic separation moieties, such as reverse phase (H4-mimic reversed phase chromatography with C16 functionality), normal phase (NP20-mimic normal phase chromatography with silicate functionality), ion exchange (e.g. CM10-weak cation exchange, with carboxylate functionality with updated hydrophobic barrier coating; WCX2-weak cation exchange with carboxylate functionality; Q10-strong anion exchange with quaternary amine functionality, with hydrophobic barrier coating; SAX2-strong anion exchange with quaternary amine functionality), immobilized affinity capture (IMAC, e.g. IMAC 30-immobilized affinity capture array with nitriloacetic acid (NTA) surface, with hydrophobic barrier coating; IMAC 3-immobilized affinity capture array with nitriloacetic acid (NTA) surface), mixed mode media (H50-binds protein through reverse phase or hydrophobic interaction chromatography with an updated hydrophobic barrier coating), Surface Enhanced Neat Desorption (SEND), and gold chip. Examples of other chip surfaces that may be used in accordance with the present invention are disclosed in U.S. patent application 2005/0090016[19]. Chips made from gold, stainless steel or inert metal can be manufactured in house with the physical specifications defined by the chipreader.

Surfaces such as these, with broad binding properties are typically used in protein profiling studies and biomarkers discovery (e.g. where samples from diseased and normal subjects are compared). As well known in the art, biomolecules bind to these surfaces through electrostatic, hydrophobic, coordinate covalent bond or Lewis-acid/base interactions. Of course other types of array surfaces exist and may be used in accordance with the present invention.

In addition to standard chromatographic surfaces, arrays may be created using virtually any molecules of interest covalently linked to the surface including antibodies, enzymes, ligands, receptors, DNA and lectins. Therefore, as opposed to standard chromatographic media, these specific surfaces can provide much more enrichment of captured analytes due to high specificity of biomolecular interactions. Thus, pre-activated arrays designed specifically for immunoassay, receptor-ligand binding and DNA-binding protein applications are also compatible with the method of the present invention. Non-limiting examples of these chips include RS100, PS10 and PS20 (Ciphergen).

Thus, depending on the properties of the sample to be analyzed, the appropriate protein chip surface will be selected in accordance with well-known principles of protein separation and identification techniques.

After binding of the proteins/peptides present in the sample to the protein chip surface, the active surface on the chip is washed with buffers having the desired stringency. The wash (or washes) allows for the removal of analytes with weak surface interaction potential and permits the enrichment of the sample with proteins/peptides having strong surface affinity. Thus, proteins or peptides with shared physical and chemical properties are retained.

Of course, in accordance with well-known principles of protein separations, the appropriate binding (conditioning) and washing buffers should be selected in order to allow the binding and retention of target biomolecules on the specific protein surface. For example, the pH and salt concentration of the wash buffer will alter the profile of the peptides retained on the ion exchange surface. Thus, one would adapt these parameters for selecting/retaining the appropriate protein on the chip surface for analysis.

In one embodiment all steps leading to sample analysis are performed directly on a chip. In another embodiment one or more sample purification step(s) is/are performed prior to on-chip analysis. In yet another embodiment an additional wash is performed prior to MS analysis in order to remove components on the chip (e.g. salts present in the buffer) that could interfere with mass spectroscopy (e.g. generally, when working with a SAX2 protein chip, a final wash is necessary when using phosphate or borate buffer). Thus, depending on the type of chip surface and buffer used, it may be necessary or preferable to add one or more wash(es) (e.g. with water or suitable buffer), which would remove MS interfering components.

For example, chemicals are known to interfere with co-crystallization or suppress sample ionization during mass analysis in the protein chip reader. Other chemicals may interfere with binding to the surface of the protein chip array, depending on the specific surface chemistry being used. Compounds may also interfere with enzymatic reactions that are performed on the chip. Thus, the required additional wash or washes may be introduced before any step which would otherwise be affected by the remaining interfering components.

For example, salts may reduce binding to ionic surfaces but can increase binding through hydrophobic interactions. Thus, one skilled in the art will choose buffers and wash conditions in accordance with the specific requirements of the protein chip used. With most, but not all, protein chip surfaces used, a water wash must be performed prior to EAM (energy absorbing molecule) addition. Guidelines for each specific type of protein chip commercialized by Ciphergen are available in their "Protein System Users Guide". Non-limiting examples of chemicals that can interfere with MS analysis include ionic detergents, high salts concentrations, polyethylene glycol (PEG), glycerol, diethylpyrocarbonate (DEPC) and dithiothreitol (DTT).

As mentioned above, in many cases ionic detergents will suppress ionization of a protein sample. In particular, proteins that have been boiled in SDS may not be easily detected. Thus, if detergents are necessary for sample extraction or sample solubilization, non-ionic detergents, such as Triton™ X-100, n-octyl β-D-glucopyranoside (OGP), Nonidet™ P40 (NP40), or dodecylmaltoside would be preferred. In general, a final concentration of up to 1% is acceptable. Of course, the final acceptable concentration depends on the type of detergent used and the protein(s) of interest. Alternatively, the interfering detergent may be removed prior to sample application on the protein chip by any well known techniques or even removed after sample application by performing one or more additional wash(es), provided that the protein chip surface used allows such a procedure (e.g. if the detergent does not interact too strongly with the protein chip surface used).

In their native state, proteins acquire a specific three-dimensional structure. The linear sequence of amino acids folds upon itself to form a specific native structure. Prior to performing a variety of protein chemistry reactions it is often necessary to denature a protein, resulting in an unfolded conformation, which is more susceptible to the subsequent chemical reactions. Proteins can be denatured by a variety of chemical and other treatments. For example, adding sufficient urea or guanidine—hydrochloric acid (HCl) to a protein solution can result in protein denaturation. A better solvent for both solubilization and denaturation is trifluoroethanol (TFE). It produces a greater sequence coverages of proteins in most cases. Non-limiting examples of treatments for protein denaturation that can be used in accordance with the present invention include heat, change of pH (acid or alkali), trifluoroethanol, urea, guanidine—HCl, dithiothreitol (DTT), dithioerytritol (DTE), β-mercaptoethanol, inorganic salts (lithium bromide, potassium thiocyanate, sodium iodide), organic solvents (ethanol, methanol, trifluoroethanol, formamide, dimethylformamide, dichloro and trichloroacetic acids and their salts), detergents (sodium dodecyl sulphate), high pressure, ultrasonic homogenisation. Of course the choice of the particular denaturing process or chemical agent to be used will depend on the type of sample (e.g. the structural properties of the protein(s) to be analyzed, etc.) and on the information that is sought. In addition, the denaturing parameters (reaction time, amount of denaturant, denaturing buffer to be used etc.) should be adapted to suit the amount and type of sample that is to be denatured and the particular protein chip surface that is used, as well known in the art.

A common naturally occurring posttranslational modification (a chemical modification occurring after protein synthesis) of many proteins is the formation of covalent disulfide bonds between cysteine residues. The formation of such disulfide bonds results in a more rigid protein structure with decreased flexibility. Proteins having disulfide bonds are less susceptible to a number of chemical reactions. Thus, for many applications, it is often desirable to cleave a protein into a number of smaller fragments. In order to cleave proteins having disulfide bonds efficiently, it is often necessary first to reduce the disulfide bonds. This is normally achieved by chemical reduction of the disulfide bonds with an appropriate reagent. Non-limiting examples of protein reducing agents compatible with the methods of the present invention include dithiothreitol (DTT), dithioerytritol (DTE), cysteine, β-mercaptoethanol, β-mercaptoethylamine, reduced glutathione, thioglycolic acid and tributylphosphine. Of course, one skilled in the art would appreciate that the above list is not extensive and most low molecular weight thiols would be effective reducing agents that can be used in accordance with the present invention. Of course the choice of the particular reducing agent to be used will depend on the type of sample (e.g. number of disulfide bonds present, the structural and physicochemical properties of the protein(s) to be analyzed etc.) and on the information that is sought. In addition, the chemical reduction parameters (reaction time, amount of reducing agent, temperature to be used etc.) should be adapted to suit the amount and type of sample that is to be reduced and the particular protein chip surface that is used, as well known in the art. It should be noted that the reduction step may be left out altogether in cases where a particular protein of interest does not contain any cysteine residues and/or disulfide bonds.

Of course the method of the present invention should be adapted in order to allow sample binding to the chip and MS analysis. Thus, when required, appropriate sample treatments and washes should be performed. For example, DTT is commonly used to reduce disulfide bonds in protein but residual DTT interferes with analysis of protein chip technology. Weak (millimolar) solutions of β-mercaptoethanol may be used in accordance with the present invention, in place of DTT for disulfide bond reduction. Alternatively, washes enabling removal of residual DTT may be performed.

Once reduced, several chemical agents may be employed to block the reduced cysteine residues through a process known as alkylation, avoiding the reformation of undesirable disulfide bonds. In accordance with the present invention, alkylating agents compatible with our approach include iodoacetamide, iodoacetic acid, ethyleneimine, 4-vinylpyridine and acrylamide. The particular alkylating agent employed often depending on some secondary purpose, for example, to enhance the solubility properties in a given medium, to produce a site subject to proteolysis by a suitable protease such as trypsin, or to provide a reversible protecting group for the cysteine thiol. In addition, the toxicity of the alkylating agent may be considered for reasons of safety, for example, acrylamide is a toxic substance readily absorbed through the skin that is reasonably anticipated to be a human carcinogen. The choice of the particular alkylating agent to be used will also depend on the type of sample (e.g. number of disulfide bonds present, the structural properties of the protein(s) to be analyzed etc.) and on the information that is sought. In addition, the alkylating parameters (exposure to light during reaction, reaction time, amount of alkylating agent, alkylation buffer, alkylation temperature to be used etc.) should be adapted to suit the amount and type of sample that is to be alkylated and the particular protein chip surface that is used, as well known in the art.

Proteins are often isolated from nature as glycoproteins. Protein glycosylation is important for the proper function of a number of proteins as well as intercellular communication and other biological phenomena. Altered sugar structures have been associated with a number of diseases including autoimmune disease and cancer[20,21]. A glycoprotein is a protein that has sugars chemically bound to specific amino acids of the protein. The sugar moiety can be a simple monosacharide or a complex structure composed of several different sugars covalently bound to each other in a variety of branched structures. Often the sugar structures are heterogeneous at a particular glycosylation site, which adds an increased level of complexity in the structural and functional characterization of the glycosylated moieties. These sugar side chains can account for anywhere from less than 1% up to 80% of the glycoprotein structure. Sugars are normally added to proteins at specific consensus sites e.g. Asparagine Xxx Threonine/Serine (where Xxx is any amino acid other than Proline) for N-linked glycosylation on the Asparagine residue.

Sugar moieties can also be bound at the hydroxyl group of Ser and Thr residues in what is known as O-linked glycosylation. Fetuin provides an example of a complex N-linked and O-linked glycoprotein having several glycosylation sites. The study of protein glycosylation is a technically challenging field and mass MS methods are increasingly being used. For example, a new consensus sequence was only recently confirmed as an Asparagine Asparagine Cysteine glycosylation site for the epidermal growth factor receptor (EGFR) expressed in human cells[22]. This discovery is of paramount importance because signaling through the epidermal growth factor receptor plays a vital part in many cancers. An accurate molecular description of the epidermal growth factor receptor, including its glycosylated moieties, may be crucial to our ability to treat the disease. The method of the present invention can be used to characterize the glycosylated portion of glycoproteins. Protein deglycosylation directly on the chip surface can be performed by chemical and enzymatic means. The mass of the protein can be measured before and after deglycosylation indicating the degree of glycosylation. For instance, neuraminidase can be used to remove terminal sialic acid residues from glycoproteins. Several enzymatic deglycosidases may be used in accordance with the present invention. Non-limiting examples include N-glycosidase F (PNGase F), endoglycosidase H (endo H), endoglycosidase F (endo F), O-glycosidase and neuraminidase. Reagents for chemical deglycosylation can also be used including hydrofluoric acid (HF)-pyridine and anhydrous pyridine. Of course, the choice of the particular endoglycosidase used will depend on the information that is sought. More than one deglycosylation step may also be performed in accordance with the present invention. For example a direct on-chip PNGase F treatment, which removes all common classes of N-glycans may be followed by a neuraminidase treatment that releases specific O-linked carbohydrates (i.e. specific forms of N-acetyl-neuraminic acid).

Protein phosphorylation is an exceedingly important cellular phenomenon directly linked to cancer, cardiovascular diseases, neural function, memory, etc. An estimated one third of proteins present in a given mammalian cell are phosphorylated at any time. Abnormal protein phosphorylation is either a cause or consequence of disease, while normal protein phosphorylation is required for normal cellular function[23]. Proteins are often isolated from nature with phosphorylated serine, threonine and tyrosine residues. The identification and characterization of protein phosphorylation is technically challenging. For example, chicken ovalbumin is a phosphoprotein for which a crystal structure was reported in 1990[24]. The structure revealed the presence of two phosphorylation sites. However, only recently using MS techniques has the presence of two additional phosphorylation sites been found[25].

Phosphoproteins can be identified and characterized directly on-chip using the method of the present invention. Protein dephosphorylation directly on the chip surface can be performed by chemical and enzymatic means. The mass of the protein can be measured before and after dephosphorylation, indicating the extent of protein phosphorylation. For on-chip enzymatic dephosphorylation, phosphatases (acid or alkaline) may be used in accordance with the present invention. Chemical dephosphorylation using HF, HF-pyridine, or other known reagents, can also be performed directly on-chip.

Once all the desired chemical and enzymatic reactions are performed, the spots on the chip are dried and a matrix solution (comprised of energy absorbing molecules (EAM), allowing energy to be transferred to the analyte i.e. proteins or peptides) is added for MS analysis. The EAM assists in the desorption and ionization of the analyte. The EAM is generally applied in organic solvent, solubilizing many proteins on the protein chip surface. As the EAM solution dries, the proteins co-crystallize with the EAM. These crystals absorb the laser energy and generate the ionized proteins detected by a protein chip reader. Any matrix solution allowing MS analysis can be used in accordance with the present invention. Non-limiting examples include saturated sinapinic acid, cyano hydroxyl cinnamic acid (CHCA), EAM 1 (Ciphergen), dihydroxybenzoic acid (DHBA), suitable derivatives of cinnamic acid and mixture thereof. Other suitable energy absorbing molecules are known to those skilled in the art. In general, the EAM is chosen based on the molecular weight of the analyte of interest. For example, saturated sinapinic acid is recommended for proteins of 15 kDa or greater while CHCA is especially good for smaller molecules.

In one particular embodiment, a PAP pen (Zymed miniPAP pen cat. no. 00-8877) can be used to circle the spots on the chip in order to prevent sample spreading during matrix addition. The pen is particularly useful with array surfaces that do not have a hydrophobic coating. It provides a water-repellent barrier that prevents solutions from bleeding off the chemically active spots of the protein chip array.

Virtually any type of protein/biological sample can be used in accordance with the present invention. Non-limiting examples include blood, serum, plasma, urine, cerebrospinal fluid (CSF), synovial fluid, nipple aspirate, seminal fluid, tears, hemofiltrate, amniotic fluid, cells or tissue homogenate, cell culture media, purified proteins etc. The biological sample may be treated to physically disrupt tissue or cell structure, thus releasing intracellular components into a solution which may further contain enzymes, buffers, salts, detergents, and the like which are used to prepare the sample for analysis. The sample may be purified or semi purified before performing on-chip analysis depending on the specific experimental requirements. Crude samples may also be used, provided that they do not contain interfering components that cannot subsequently be removed from the chip prior to performing the method step with which it interferes (e.g. MS analysis). Of course, synthetic (e.g. synthetic peptides) or semi-synthetic samples can also be used.

The methods of the present invention is optimized by testing several types of chip surfaces in order to determine which surface gives the best results with a particular type of sample and particular chemical and enzymatic steps performed. Thus, a person skilled in the art could carry out the method of the present invention on 2, 3, 4, 5, 6 or more chip surfaces in parallel and determine which surface gives the best results. Similarly, several chips having the same surfaces could be tested in parallel to determine the optimal binding and washing buffers as well as the optimal incubation time, concentration of sample, reagents, etc, as well known in the art.

Once all chemical reactions are performed, a MS analysis is conducted to identify the biomolecules of interest. Any suitable MS device may be used in accordance with the present invention as long as it allows proteins/peptides on the substrate to be resolved. Similarly, the measured peptides/proteins can be compared to peptide masses, product ion spectra, or sequence query from in silico digestion of the protein database using any search engine available (e.g. ProFound™, Mascot™, Aldente™, Phenyx™, PeptideMapper™, PeptideSearch™ and the like).

The development of two "soft" ionization techniques for the ionization of non-volatile molecules have proven crucial for the development of methods for identification and structure analyses of biological macromolecules. These two ionization techniques are matrix assisted laser desorption ionization (MALDI) which was described approximately one year after a related report of laser desorption ionization introduced in 1988 by Tanaka[3] and electrospray ionization[2]. Together, the two techniques have made the precision and sensitivity of mass spectrometry readily available for the study of biomolecules and their reactions. As an example, the mass of proteins of a molecular weight exceeding 100 kDa can be readily measured with high sensitivity and accuracy. Currently, there are no other techniques than can achieve comparable results.

Although not essential, a laser desorption time-of-flight (TOF) mass spectrometer is preferably used for MS analysis in accordance with the present invention. Because of their design features, laser desorption ionization and time-of-flight (TOF) mass spectrometry are complementary and are preferably used. In laser desorption mass spectrometry, a sample containing proteins/peptides is applied to a substrate or a probe and introduced into an inlet system. The proteins/peptides are desorbed and ionized into the gas phase with a laser pulse in the ionization source. The ions generated are sampled into the mass spectrometer by ion optic lenses, and then in a time-of-flight mass analyzer, all ions are accelerated with equal force through a short high voltage field and allowed to drift through a high vacuum chamber. At the opposite end of the high vacuum chamber, the accelerated ions are detected by a sensitive detector surface, with each of the different ions arriving at different times. The time-of-flight is a function of the velocity of the ions, which is dependent on the ratio of mass/charge. By measuring the elapsed time between ion formation and ion detector impact, the presence or absence of proteins/peptides of specific mass to charge ratio can de determined.

Matrix-assisted laser desorption/ionization mass spectrometry (MALDI-MS) is a method of mass spectrometry involving the use of an energy absorbing molecule (sample matrix) that permits the desorption of intact proteins or peptide fragments from a laser pulsed probe surface. MALDI is described in U.S. Pat. No. 5,118,937[26] and U.S. Pat. No. 5,045,694[27]. The sample is mixed with the MALDI matrix material and placed on the surface of an inert probe.

Commonly employed absorbing molecules include cinnamic acid derivatives, sinapinic acid (SPA), cyano hydroxy cinnamic acid (CHCA) and dihydroxybenzoic acid (DHBA). Other suitable energy absorbing molecules can be used by those skilled in this art. The liquid mixture of MALDI matrix material and sample containing proteins/peptides is allowed to dry forming crystals of encapsulate analyte molecules. The sample is then irradiated for MALDI-MS analysis. The method is useful for detecting proteins/peptides as described in this invention.

Surface-enhanced laser desorption ionization mass spectrometry (SELDI-MS) is a derivative of MALDI that allows the fractionation and detection of proteins/peptides in complex mixtures. In SELDI-MS, proteins/peptides are bound to the surface of a protein chip by retentate chromatography due to the physicochemical properties of the chip surface. Non-bound molecules (salts and other interfering molecules) are washed from the probe surface using appropriate buffers before MS analysis. SELDI is described in: U.S. Pat. No. 5,719,060[4]; U.S. Pat. No. 6,225,047[5] and Weinberger et al., (2000)[6].

Proteins on the chip surface can be desorbed and ionized by laser desorption ionization for MS analysis. Any suitable mass spectrometer can be used provided it allows the analytes to be appropriately resolved. Thus, once the desired chip chemistries have been developed, the chip can be read by laser desorption ionization coupled to a variety of mass spectrometers including a time-of-flight (TOF) of low or high resolution, quadrupole, iontrap MS (IT), Fourrier Transform MS (FTMS) and sector instruments. In addition, the chip can be read followed by analysis on a variety of tandem mass spectrometers such as a triple quadrupole or TOF-TOF as well as a hybrid tandem instrument such as a quadrupole-TOF. The advantage of the tandem instruments is the ability to select a particular precursor ion in the first sector followed by fragmentation and analysis of the fragments on the second sector yielding information regarding the structure of the compound such as sequence information of peptides. The ITMS and FTMS can also be used for fragmentation analysis as these instruments can capture specific ions with subsequent fragmentation and analysis of the fragments.

For optimal results, the chip holder can be placed in tandem, on the front of a high resolution MDS/Sciex QSTAR or Micromass QTOF mass spectrometer. The sample is read as it would normally be analysed with a low resolution TOF instrument but the added advantages associated with the high performance mass spectrometer would be realized. The superior quality of data obtained from such an instrumental configuration can reveal a number of characteristics about the sample that are not easily discernable with a low resolution mass spectrometer. For example, exact mass measurements with less than 5 ppm error are often sufficient to confirm the presence of a specific amino acid residue or adduct. In addition, the QSTAR and QTOF are "tandem" mass spectrometers that can be used for peptide sequencing in ms/ms ion mode where searches can be performed on commercial databases (e.g. Mascot, Matrix science, UK) for rigid identification of compounds or sites of chemical and posttranslational modification not attainable with PMF searches. Currently, Ciphergen Biosystems offers a Tandem MS PCI protein chip Interface system for compatibility with MDS/Sciex QSTAR mass spectrometers. This configuration is extremely powerful in conducting high performance low molecular weight proteome phenotyping or protein-protein interaction in drug development, drug and biomarker discovery. Another application is in the study of ligand-receptor identification or in capturing antibodies if appropriate chips are utilized. The present invention utilizes the said configuration as shown in examples to follow. An application employing such a configuration has been reported[28].

In order to provide a clear and consistent understanding of terms used in the specification and claims, including the scope to be given such terms, a number of definitions are provided herein below.

Unless defined otherwise, the scientific and technological terms and nomenclature used herein have the same meaning as commonly understood by a person of ordinary skill to which this invention pertains. Commonly understood definitions of molecular biology terms can be found for example in Dictionary of Microbiology and Molecular Biology[29], The Harper Collins Dictionary of Biology[30], Glossary of genetics: Classical and molecular[31]; Molecular Biology of the Cell[32] and Genes VII[33]. Generally, the procedures of sample/protein purification and separation, protein chip utilization, MS analysis, molecular biology methods and the like are common methods used in the art. Such standard techniques can be found in reference manuals such as for example Sambrook et al. (2000)[34], Ausubel et al. (1994)[35], Laemmli, U.K. (1970)[36]. Practical protein chemistry, A handbook[37], M P Washburn et al., (2001)[38], Yates J R III (2004)[39]; Industrial proteomics Applications for Biotechnology and Pharmaceuticals[40], Karas, M and Hillenkamp F (1988)[41].

DEFINITIONS

The use of the word "a" or "an" when used in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term about.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the twenty natural amino acids and their abbreviations follow conventional usage. Stereoisomers (e.g., D-amino acids) such as α,α-disubstituted amino acids, N-alkyl amino acids, lactic acid and other unconventional amino acids may also be suitable components for the polypeptides of the present invention. Examples of unconventional amino acids include but are not limited to selenocysteine, citrulline, ornithine, norvaline, 4-(E)-butenyl-4(R)-methyl-N-methylthreonine (MeBmt), N-methyl-leucine (MeLeu), aminoisobutyric acid, statine, N-methyl-alanine (MeAla).

As used herein, "protein" or "polypeptide" means any peptide-linked chain of amino acids, regardless of posttranslational modifications (e.g. phosphorylation, glycosylation, sulfation, acetylation, sumoylation, prenylation, ubiquitination etc).

As used herein, the term "purified" refers to a molecule (e.g. polypeptides or proteins) having been separated from a component of the composition in which it was originally present. Thus, for example, a "purified protein or polypeptide" has been purified to a level not found in nature. A "substantially pure" molecule is a molecule that is lacking in most other components (e.g., 30, 40, 50, 60, 70, 75, 80, 85, 90, 95, 96, 97, 98, 99, 100% free of contaminants). By opposition, the term "crude" means molecules that have not been separated from the components of the original composition in which it was present. Therefore, the terms "separating" or "purifying" refers to methods by which one or more components of the biological sample are removed from one or more other components of the sample. Sample components include nucleic acids in a generally aqueous solution that may include other components, such as proteins, carbohydrates, or lipids. A separating or purifying step preferably removes at least about 70% (e.g., 70, 75, 80, 85, 90, 95, 96, 97, 98, 99, 100%), more preferably at least about 90% (e.g., 90, 91, 92, 93, 94, 95, 96, 97, 98, 99, 100%) and, even more preferably, at least about 95% (e.g., 95, 96, 97, 98, 99, 100%) of the other components present in the sample from the desired component. For the sake of brevity, the units (e.g. 66, 67 . . . 81, 82, . . . 91, 92% . . .) have not systematically been recited but are considered, nevertheless, within the scope of the present invention.

The terms "inhibiting," "reducing" or "interfering" or any variation of these terms, when used in the claims and/or the specification includes any measurable decrease or complete inhibition of at least one chemical, physicochemical, or enzymatic activity in any of the present method steps to achieve a desired result. For example, a compound is said to be interfering with MS detection when a decrease in specificity and sensitivity is measured following a treatment with the "inhibiting", "reducing" or "interfering" compound as compared to in the absence thereof. Similarly, a compound is said to be "inhibiting" an enzymatic step (e.g. dephosphorylation, deglycosylation, trypsinization, etc) of the method of the present invention when the efficiency of the enzymatic reaction is reduced or completely abolished following a treatment with the "inhibiting", "reducing" or "interfering" compound as compared to in the absence thereof.

"Probe" refers to a device that is removably insertable into a gas phase spectrometer and comprises a substrate having a surface for presenting analytes for detection. A probe can comprise a single substrate or a plurality of substrates. Terms such as protein chip, protein chip array, or chip are also used herein to refer to specific kinds of probes.

"Gas phase ion spectrometer" refers to an apparatus that measures a parameter which can be translated into mass-to-charge ratios of ions formed when a sample is ionized into the gas phase. Generally ions of interest bear a single charge, and mass-to-charge ratios are often simply referred to as mass.

"Mass spectrometer" refers to a gas phase ion spectrometer that includes an inlet system, an ionization source, an ion optic assembly, a mass analyzer, and a detector.

"Laser desorption mass spectrometer" refers to a mass spectrometer which uses a laser as an ionization source to desorb an analyte.

"Binding functionalities" refer to functional group(s) of a protein chip surface material that bind analytes. Binding functionalities can include, but are not limited to, a carboxyl group, a sulfonate group, a phosphate group, an ammonium group, a hydrophilic group, a hydrophobic group, a reactive group, a metal chelating group, a thioether group, a biotin group, a boronate group, a dye group, a cholesterol group, derivatives thereof, or any combinations thereof. Binding functionalities can further include other adsorbents that bind analytes based on individual structural properties, such as the interaction of antibodies with antigens, enzymes with substrate analogs, nucleic acids with binding proteins, and hormones with receptors.

"Analyte" refers to a component of a sample which is desirably retained and detected. The term can refer to a single component or a set of components in the sample.

"Conditioned" as applied to the present invention relates to adaptation or modification of a substrate surface (protein chip surface) to promote adhesion of analytes onto the substrate surface.

"Energy absorbing molecule" or "EAM" refers to a molecule that absorbs energy from an ionization source in a mass spectrometer thereby enabling desorption of analyte from a probe surface. Energy absorbing molecules used in MALDI are frequently referred to as "matrix." Cinnamic acid derivatives, sinapinic acid ("SPA"), cyano hydroxy cinnamic acid ("CHCA") and dihydroxybenzoic acid are frequently used as energy absorbing molecules in laser desorption of bioorganic molecules. Other suitable energy absorbing molecules are known to those skilled in this art. See, e.g., U.S. Pat. No. 5,719,060[4] for additional description of energy absorbing molecules.

Other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

Having thus, generally described the invention, reference will be made to the accompanying drawings, showing by way of illustration only an illustrative embodiment thereof and in which:

FIGS. 2c and 2d show 1 μg EGFRED on NP20 chip before and after deglycosylation respectively.

DETAILED DESCRIPTION OF ILLUSTRATIVE EMBODIMENTS

Figure 1:
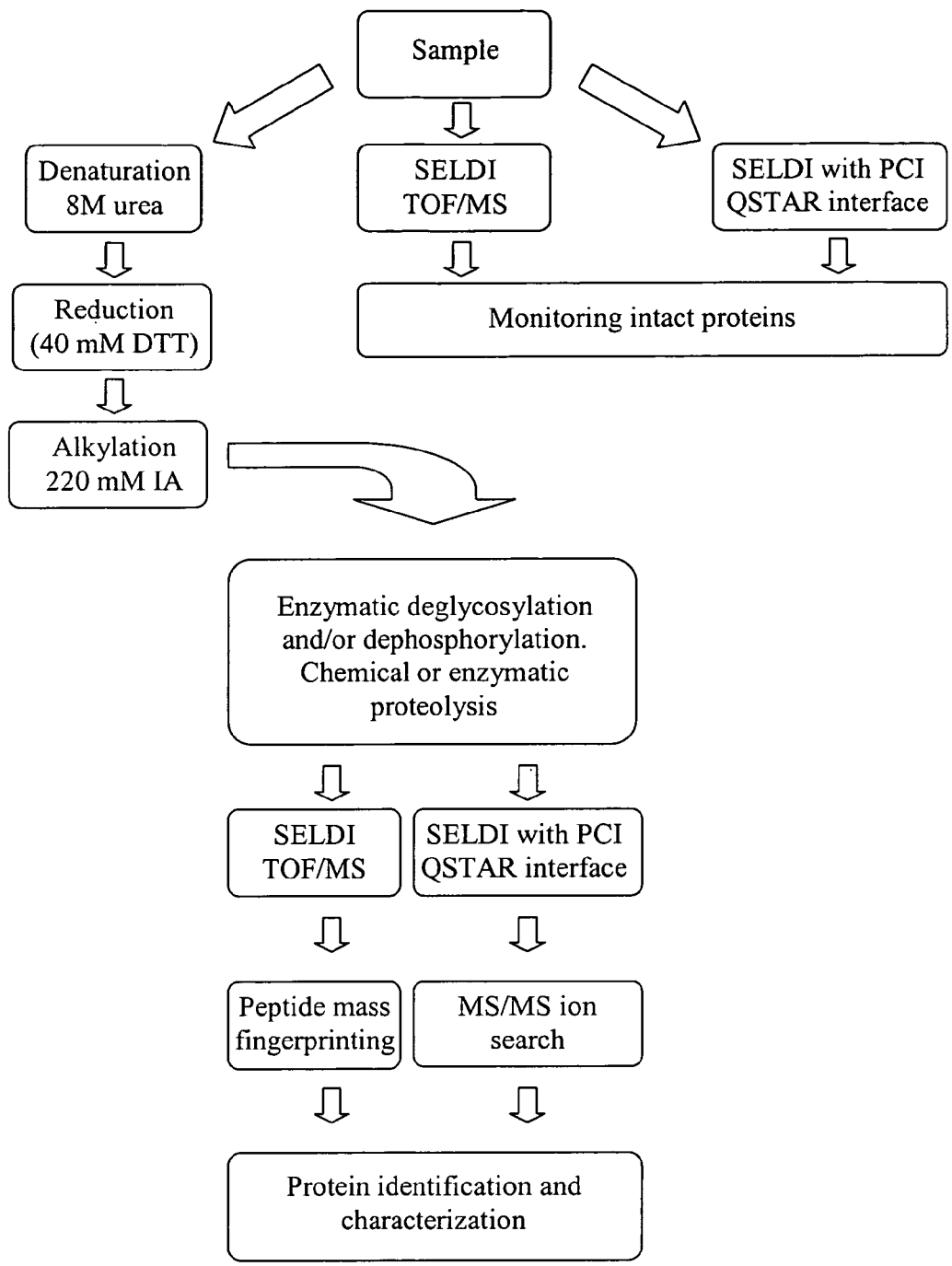
FIG. 1 shows a typical strategy for on-chip protein analysis. The schematic shows the steps that were followed to monitor deglycosylation and dephosphorylation reactions and for identification of proteins investigated. The difference in molecular masses reflects the degree of glycosylation and phosphorylation in the molecules.
Figure 4:
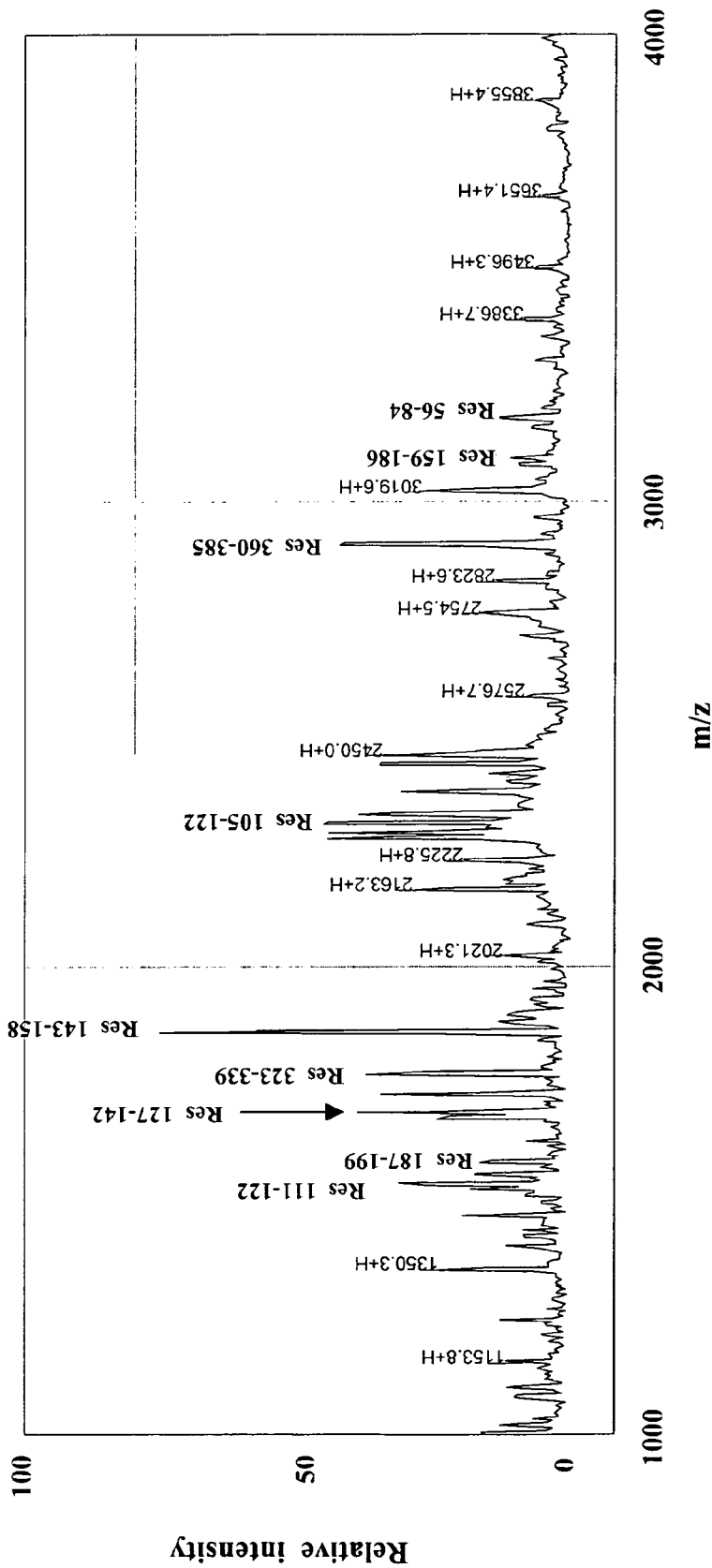
FIG. 4 shows a mass spectrum of 1 µg ovalbumin after its on-H4 chip denaturation, reduction, alkylation, deglycosylation and tryptic digestion. Some of the identified sequences are shown.

Here, processes combining chemical and enzymatic treatments directly on-chip to monitor various protein modifications such as deglycosylation and dephosphorylation reactions, and identify proteins using PMF were examined. Three representative proteins were selected based on their complexity and physico-chemical features (Table 1). Two other proteins found in rat urine were also analysed. All linear protein sequences are shown in FIG. 4. The signal and propeptide regions are removed when applicable. Their posttranslational modifications are shown in table 1 and described in the text. The hydrophobicity of the proteins will determine how tightly they are bound to the chromatographic surface on the chip and the wash cycle chosen to remove impurities is dictated by this interaction. An outline of the general procedure developed for chemical and enzymatic treatment of proteins and peptides is shown in FIG. 1. This approach allowed to adapt different sequences of reactions according to the characteristics of the proteins and the nature of their modifications.

C, bovine serum albumin, bovine insulin) were also analysed and produced excellent sequence coverages (over 81%). Based on the performance of the methods of the invention with the three complex proteins listed above, the present invention is amenable to any protein of interest.

The present invention is illustrated in further details by the following non-limiting examples.

EXAMPLE 1

Materials and Methods

Human EGFRED (Epidermal growth factor receptor ecto domain) was a gift from Dr. J. Baardsnes of the Biotechnology Research Institute, National Research Council of Canada, Montreal, Canada. Cesium Iodide/octapeptide mixture and reserpine were gifts from MDS Sciex, Toronto, Canada. Trypsin was obtained from Boehringer Mannheim (Ingelheim, Germany) and used without further purification. Urea, ammonium bicarbonate, α-cyano-4-hydroxy-cinnamic acid (CHCA), sinapinic acid (SPA), dithiothreitol (DTT), iodoacetamide(IA), 2,2,2-trifluoroethanol (TFE), adrenocorticotropic hormone (ACTH), polypeptide P14R, alkaline phosphatase (ALP), chicken ovalbumin, chicken lysozyme, bovine insulin, bovine serum albumin, horse cytochrome C, bovine fetuin and cyanogen bromide were obtained from Sigma (St. Louis, Mo.). Trifluoroacetic acid (TFA) and formic acid were obtained from Pierce (Rockford, Ill.). Neuraminidase, N-glycosidase F, O-glycosidase, endoproteinases Arg-C, Asp-N, Glu-C Lys-C and pronase were purchased from Roche (Indianapolis, Ind.). Protein chips (working spot 2.5 mm diameter-H4, NP20, SAX2, WCX2, IMAC3 and Send Alpha) were purchased from Ciphergen Biosystems Inc. (Fremont, Calif.). Micro Bio-spin 6 chromatography columns were obtained from Bio-Rad (Mississauga, ON). Urine samples were collected from a male Sprague-Dawley rat treated with puromycin aminonucleoside to induce proteinuria. All solvents were HPLC grade. Aqueous solutions of the proteins, enzymes and reagents used in the experiments described below were prepared in 0.1 M ammonium bicarbonate unless otherwise indicated.

Chemical pretreatment. In the present illustrative examples hydrophylic NP20 and hydrophobic H4 chips were used. Proteins were first chemically denatured, reduced and alkylated as follows: chips were conditioned by adding 3 µL of

TABLE 1

Structural characteristics of the model proteins

| Protein | Average MW (kDa)[a] | Number of Disulfide bridge | Number of Glycosylation sites[b] | Number of Phosphorylation sites |
|---|---|---|---|---|
| Human EGFRED | 81.29 | 21 | 11-N | — |
| Bovine fetuin | 46.21 | 6 | 3-N, 3-O | — |
| Chick ovalbumin | 44.73 | 1 | 1-N | 4 |
| Alpha 2µ globulin | 18.73 | 1 | 1-N | — |
| Rat urinary albumin | 65.90 | 17 | — | — |

[a]Measured molecular weight with posttranslational modifications.
[b]Carbohydrate moieties can be attached via N— or O— linkages to the proteins.

Epidermal growth factor receptor ectodomain (EGFRED), chicken ovalbumin and bovine fetuin were selected as model proteins because of their complexity, specific physicochemical properties and posttranslational modifications (PTMs). Less complex proteins (chicken lysozyme, horse cytochrome water or acetonitrile. The selectivity of the chip varies with the organic component and/or salt concentration of the binding buffer. One µL of 1 µg/µL solution of the protein (e.g. ovalbumin, 23.4 pmol; EGFRED, 14.6 pmol; and fetuin, 26.0 pmol) was added to the chip. Denaturation was accomplished by adding 1 µL of TFE and incubating for two hours at room temperature. Disulfide bonds were reduced by adding 1 µL of 40 mM DTT with incubation in a water bath at 56° C. for 45 min. Finally, alkylation of the thiol groups was performed in a dark humidity chamber at room temperature by applying 1 µL of 220 mM iodoacetamide and allowing the reaction to proceed for 30 min. The denatured, reduced and alkylated proteins were subjected to two different enzymatic reaction schemes whereby the model proteins were 1) deglycosylated or dephosphorylated and analyzed by SELDI-TOF/MS or ABI/Sciex QSTAR MS to monitor the removal of the corresponding posttranslational modifications or 2) proteolyzed prior to PMF or product ion scan mode for identification purposes using database searching tools.

Enzymatic deglycosylation. Protein glycosylation is an important protein modification serving various functions, which are protein dependent. Glycosylation can protect a protein from degradation, retain the protein in the endoplasmic reticulum until properly folded, or direct the protein to its proper destination by serving as a transport signal. Oligosaccharides exposed on the cell surface allow different cells to recognize each other.

Deglycosylation of EGFRED and ovalbumin (N-glycan-containing proteins) was performed by depositing 1 µL of 1 Unit/µL solution of N-glycosidase F and incubating the array in a 37° C. water bath for 2 hrs.

Fetuin contains both N— and O-carbohydrate linkages. Deglycosylation reactions were performed sequentially on an H4 chip. Two experimental approaches were applied: a) monitoring of the deglycosylation reactions using denatured protein without reduction and alkylation; b) the complete set of chemical reactions described above (FIG. 1) was applied prior to performing enzymatic proteolysis. The denatured or alkylated fetuin was N-deglycosylated by spotting 1 µL of 0.5 Unit/µL of N-glycosidase F on the chip and incubating 2 hrs at 37° C. in a water bath. Conversely, O-linked carbohydrates were selectively cleaved in a two-step approach: sialyl (α-N-acetylneuraminic acid) residues were cleaved by adding 1 µL of 5 mUnit/µL neuraminidase solution and incubating for 1 hr in 37° C. water bath whereas the serine/threonine O-linked β-D-galactosamine residues were cleaved by adding 1 µL of 2 mUnit/µL of O-glycosidase and incubating the arrays for 2 hours in a 37° C. water bath.

Enzymatic dephosphorylation. Ovalbumin was denatured, reduced and alkylated as described above on an H4 chip. Dephosphorylation was performed by adding 1 µL of 2 µg/µL Alkaline phosphotase solution (0.1 M ammonium bicarbonate, 1 mM magnesium chloride) and incubating in a 37° C. water bath for 2 hrs.

Enzymatic proteolysis. Enzymatic digestion was performed following denaturation, reduction, alkylation and/or deglycosylation of the proteins on NP20 hydrophilic chips. One µL of 0.5 µg/µL trypsin solution was applied to each spot and digested for 2 hrs at 37° C. in a water bath. The array was air-dried and rinsed twice with 4 µL of water prior to adding the sample matrix. In addition to trypsin proteolysis, EGFRED was also treated with 0.5 µg of four other protease of high specificities Arg-C, Asp-N, Glu-C and Lys-C, and the non-specific protease pronase (Table 3). To differentiate the peptides generated from the digestion of the model proteins from those originating from autolysis, control experiments were conducted with all reagents and/or proteases in the absence of the proteins.

Chemical proteolysis. For preparation of on-chip chemical cleavages or 2 µg of proteins was mixed with 2 µl 0.1 M ammonium bicarbonate. Two µl of TFE was added and incubated for 1 h at room temperature. After air-drying, 1 µl of 40 mM DTT was added to the spot which was further incubated at 56° C. in a water bath for 45 min. For alkylation, 1 µl of 220 mM IA was added and further incubated at room temperature in a humidity chamber for 30 min. For BNPS-skatole cleavage, 3 µl of 50% acetic acid and 2 µl of 1.3 mg/ml BNPS-skatole were added. For BNPS-skatole and CNBr double cleavage, 2 µl of 50% TFA and 2 µl of saturated CNBr solution (>10 mg/ml) were added and the chip was incubated at 47° C. in a water bath for 10 min. The spot was air dried before rewashing with 4 µl HPLC grade water. Chips were again air dried before the addition of the CHCA matrix. For formic acid cleavage of aspartyl bonds, 200 µL of freshly prepared 2% formic acid was added. The incubation time was between 10 and 60 min. depending on the protein, followed by the addition of DDT. The chip was analyzed using the SELDI-TOF/MS or a high resolution QSTAR instrument. A summary of the peptides identified by the chemical agents and the percent sequence coverage is shown in Table 2.

TABLE 2

Proteins chemically cleaved and their agents.

| Protein | Chemical agent | Number of proteolytic peptides | % Sequence coverage |
|---|---|---|---|
| EGFRED (Acc. No. P00533, SEQ ID NO:1) | BPNS Skatole | 5 | 64.6 |
|  | Formic acid | 12 | 67.0 |
|  | CNBr | 5 | 65.1 |
| Bovine fetuin (Acc. No. P12763, SEQ ID NO:2) | BPNS Skatole | 14 | 60.8 |
|  | Formic acid | 14 | 61.3 |
| Ovalbumin (Acc. No. P1012, SEQ ID NO:3) | BPNS Skatole | 2 | 59.3 |
|  | Formic acid | 7 | 65.2 |
| Rat urinary albumin (RUA) (Acc. No. P02770, SEQ ID NO:4) | BPNS Skatole | 5 | 49.9 |
|  | Formic acid | 15 | 51.1 |
|  | CNBr | 4 | 62.2 |
| Alpha-2u-globulin (AUG) (Acc. No. P02761, SEQ ID NO:5) | Formic | 8 | 68.2 |
|  | CNBr | 3 | 74.1 |

Rat urinary proteins. Sprague-Dawley rats were administered a single 100 mg dose of puromycin aminonucleoside to induce proteinuria and urine samples were collected in plastic vials containing phenol as stabilizer at specific time intervals after administration. The samples were centrifuged to remove debris, divided in 50 µL aliquots which were frozen at −80° C. until analyzed. Samples were thawed on ice and a 25 µL aliquot was desalted with a Bio-Rad™ column. The resulting eluate was concentrated to a volume of 10 µL. The protein content in this urine sample was 0.6 µg µL$^{-1}$ by Bradford assay[42]. The concentrated sample was applied to a NP20 chip followed by denaturation, reduction, alkylation and trypsinization prior to analysis.

Mass spectrometric analysis. To deglycosylated, dephosphorylated and native samples 1 µL of saturated SPA prepared in 50% aqueous acetonitrile containing 0.5% TFA was added to each spot. For proteolyzed samples, the array was air dried and rinsed twice with 4 µL water. The washing was done by pipetting water to the chip and aspirating the water several times between the spot and the pipette tip prior to the addition of 0.5 µl of 20% CHCA in 50% aqueous acetonitrile containing 0.5% TFA to each spot. Mass spectra were generated in the positive-ion mode using a PBSII-c ProteinChip reader (Ciphergen Biosystems Inc, Fremont, Calif.). The instrument was calibrated externally with ACTH at 2.465 kDa and bovine insulin at 5.733 kDa. The average mass accuracy after external calibration of the PBSII-c is 2000 ppm (0.2%) for proteins of 10 kDa to 300 kDa and 1000 ppm (0.1%) for polypeptides of 1 kDa to 10 kDa. Resolution was greater than 700 (average) for 5 pmol of human recombinant insulin. Mascot™ (Matrix Science ltd, London U.K.) was used for protein identification based on PMF analysis.

As described briefly earlier, the chip holder can also be coupled to a high resolution mass spectrometer to collect data of higher quality. The ionspray source on a ABI/Sciex QSTAR hybrid high resolution mass spectrometer was removed and replaced by a Ciphergen chipreader. After obtaining an acceptable operating vacuum, the instrument was calibrated with reserpine (M+609.2812 amu and its characteristic fragment at 195.0657 amu). This compound was used to optimize peak shape. The octapeptide (MW 829.5398 amu)/cesium iodide (MW 132.9054 amu) mixture was used as the calibrant for the positive mode. Taurocholic acid was utilized as a calibrant to optimize the TOF section in the negative mode. The product ion spectrum was suitable for assessing product ion performance. The instrument was ready for use when the mass drift was less than 5 ppm. At that time the mass resolution was 10,500.

EXAMPLE 2

On-Chip Protein Deglycosylation

Ovalbumin is a 44.73 kDa hydrophobic glycoprotein which has a disulfide bridge, one N-glycosylation and four phosphorylation sites[22, 25, 43]. These characteristics make it an attractive example for the assessment of the on chip protein analysis of the present invention. The oligosaccharide moiety of ovalbumin is heterogeneous with an average of 1.65 kDa[43]. In the experiments performed the average molecular weight of ovalbumin as measured was decreased by 1.67 kDa to 43.06 kDa (FIGS. 2a and b) when N-deglycosylated on an H4 chip, indicating that the glycan side chain was completely removed. N-deglycosylation proceeded at a slower rate on the hydrophilic NP20 chip, as significant amounts of intact ovalbumin and a byproduct were seen. After 2 hr of reaction loss of only 1.376 kDa from ovalbumin molecular weight (data not shown), was observed. This indicates that the chemistry of both the protein and chip surface plays an enabling role in the deglycosylation reaction. One may hypothesize that the hydrophobic nature of the H4 chip and that of several segments of ovalbumin create appropriate binding conditions for deglycosylation of the $Asp_{-292}$ glycan residue, which are probably not favored on the hydrophilic NP20 chip.

Figure 2:
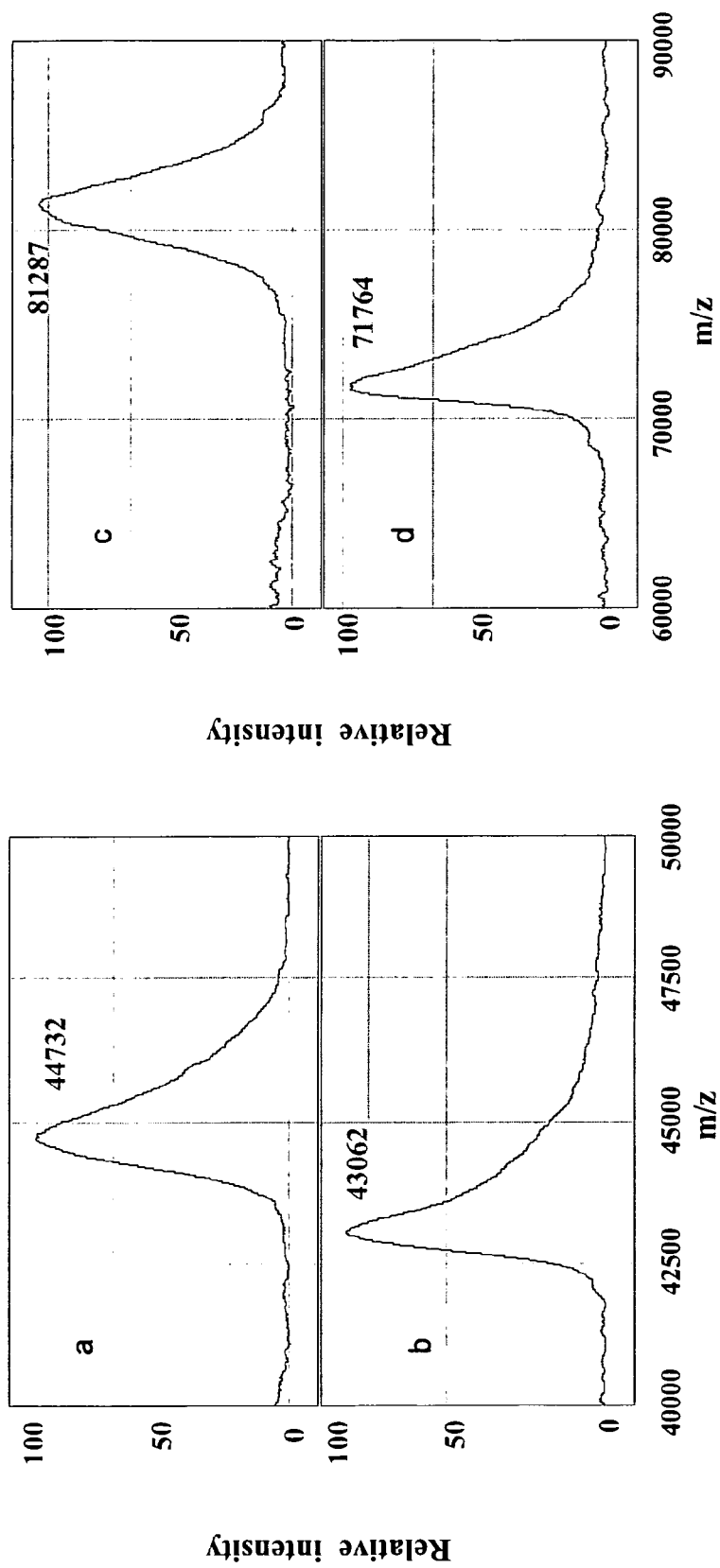
FIG. 2 shows a mass spectrum of on-H4 chip denaturation, reduction, alkylation and deglycosylation of 1 μg ovalbumin (a) before deglycosylation; (b) after deglycosylation).

Human EGFRED has eleven N-glycosylation sites with a variety of glycoforms and twenty-one disulfide bridges modulating its tertiary structure[22]. This heavily-modified protein is a prime example to verify the protocol. Alkylated EGFRED was digested with N-glycosidase F for two hours on a NP20 chip and analyzed. As shown in FIGS. 2c and 2d, a mass shift of 9.53 kDa (from 81.29 kDa to 71.76 kDa) indicates several or all glycosylation sites were removed. The reaction proceeded at a much slower rate on the H4 chip as unreacted EGFRED was still detected, even when the reaction time was extended to 3 or 4 hr.

Fetuin has three N-linked oligosaccharides, three O-linked oligosaccharide chains and a potential fourth O-linked glycan[44]. Each of the carbohydrate units attached to asparagine residues have hybrid structures with a molecular weight of approximately 2.86 kDa[45]. In the deglycosylation approach used herein, fetuin was denatured on H4 chip prior to treatment with N-glycosidase F, for two hours at 37° C. Analysis showed that fetuin was deglycosylated as its molecular mass was reduced by 5.19 kDa, from 46.21 kDa to 41.02 kDa. The O-glycosidically linked sugar side chains comprise a disialated structure with a molecular weight of approximately 950 Da[44]. All three O-linked glycosylation sites on fetuin were removed as its molecular weight decreased by approximately 3.00 kDa when treated with neuraminidase and O-glycosidase.

EXAMPLE 3

On-Chip Protein Dephosphorylation

Most aspects of cell life are regulated by protein phosphorylation; abnormal phosphorylation can result in or be caused by disease[23]. At any moment roughly 30% of all mammalian proteins are phosphorylated[23]. This reversible reaction is regulated by the concerted actions of protein kinases and phosphatases, which affect phosphorylation and de-phosphorylation respectively.

Figure 3:
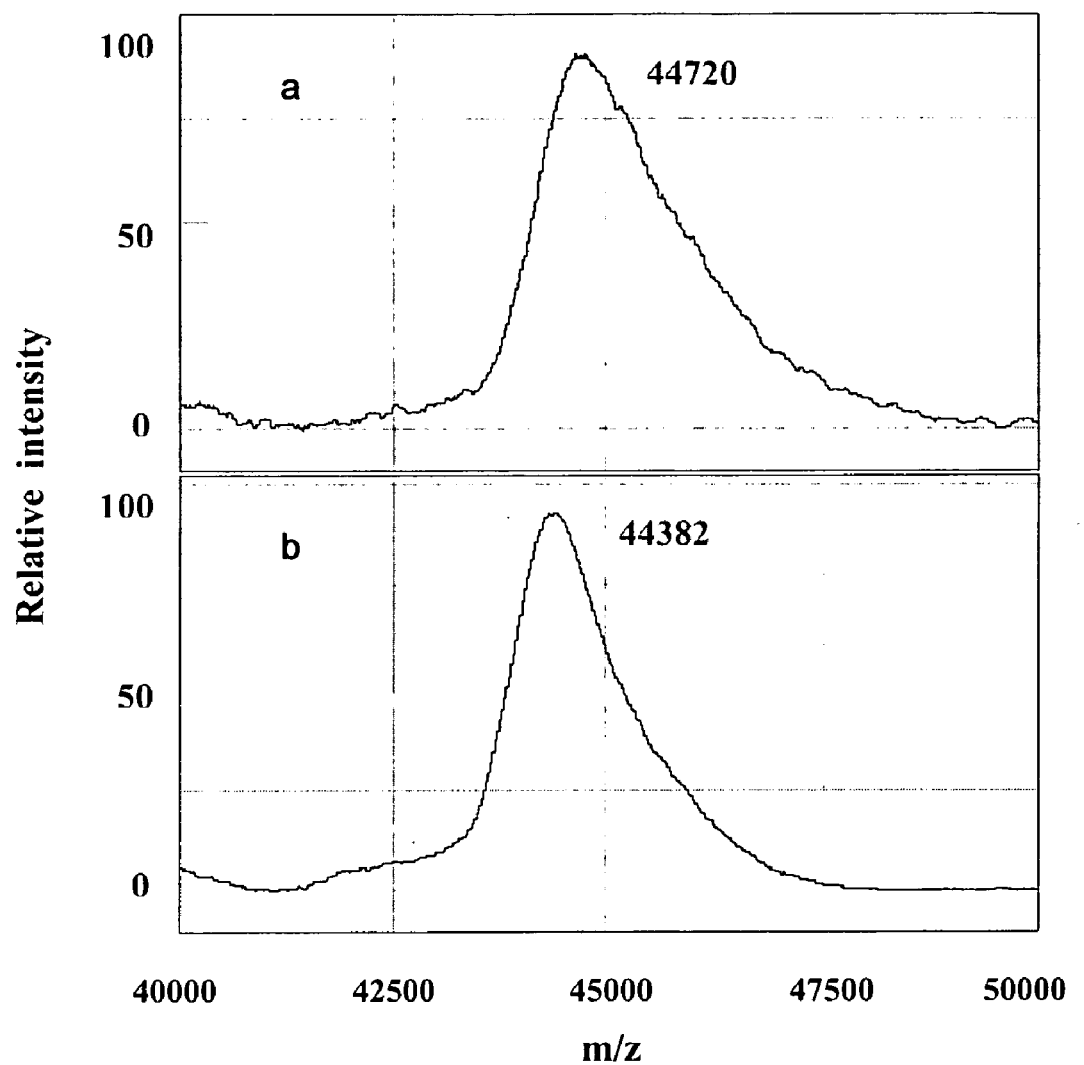
FIG. 3 shows a mass spectrum of on-H4 chip denaturation, reduction, alkylation and dephosphorylation of 1 μg ovalbumin (a) before dephosphorylation;(b) after dephosphorylation). The presence of four phosphate groups is quite evident.

Ovalbumin, with its four phosphoserine sites, was chosen to investigate protein dephosphorylation. This process resulted in a mass difference of approximately 338 Da less than native ovalbumin, which corresponds to the removal of the four phosphate molecules (FIG. 3). Similarly to results mentioned above for the N-deglycosylation reaction, negligible dephosphorylation activity was observed when using the NP20 chip even when increasing phosphatase concentration and/or extending reaction time (data not shown). This suggests that chips with a hydrophobic surface are probably more suitable than hydrophilic chips for performing enzymatic treatment of proteins with a hydrophobic backbone such as ovalbumin.

EXAMPLE 4

On-Chip Proteolysis

Trypsinization of denatured, reduced and alkylated ovalbumin generated a complex peptide profile. This was not surprising because of the complexity of the native hydrophobic protein. Proteolysis was only efficient when ovalbumin was first deglycosylated on H4 chips according to the sequence of reactions presented in FIG. 1. Deglycosylated ovalbumin was subsequently trypsinized and analyzed (FIG. 4). In this particular case, the mass tolerance of the mascot search program was set at 2 Da. Fourteen peptides, corresponding to 60% coverage of the protein amino acid sequence (Table 3) were matched with their predicted peptides from the in-silico digestion. The search results identified chicken ovalbumin among a relatively complex mixture of peptides originating not only from ovalbumin, but also from N-glycosidase F and trypsin. This on-chip method provided sequence coverage similar to that obtained from in-solution digestion and is an elegant and flexible approach to the characterization of proteins with oligosaccharide substituents.

Figure 5:
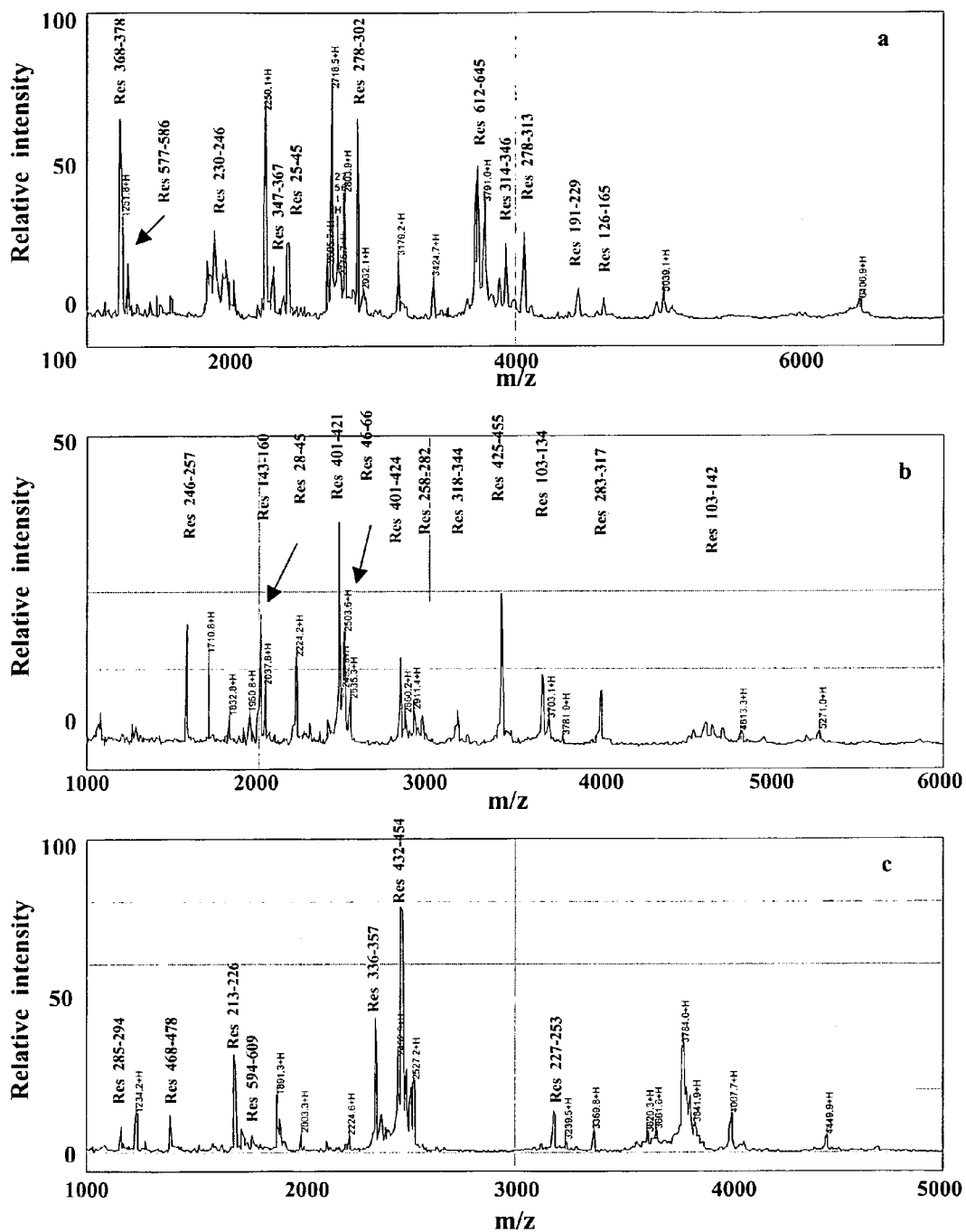
FIG. 5 shows a mass spectrum of 1 µg EGFRED after its on-NP20 chip denaturation, reduction, alkylation, deglycosylation with a) Asp-N digestion, b) Glu-C digestion, c) Lys-C digestion.

EGFRED was treated on-chip through a sequence of five chemical and enzymatic steps. The proteolytic reaction were performed using trypsin, Arg-C, Asp-N, Glu-C, Lys-C and pronase. Typical mass spectra are presented in FIGS. 5a, 5b and 5c. Each of the proteolytic reactions generated specific peptides. EGFRED was identified by PMF with confident scores, and also with product ion search. The sequence coverages were also excellent. Results of the database search are summarized in Tables 2 and 3.

Figure 6:
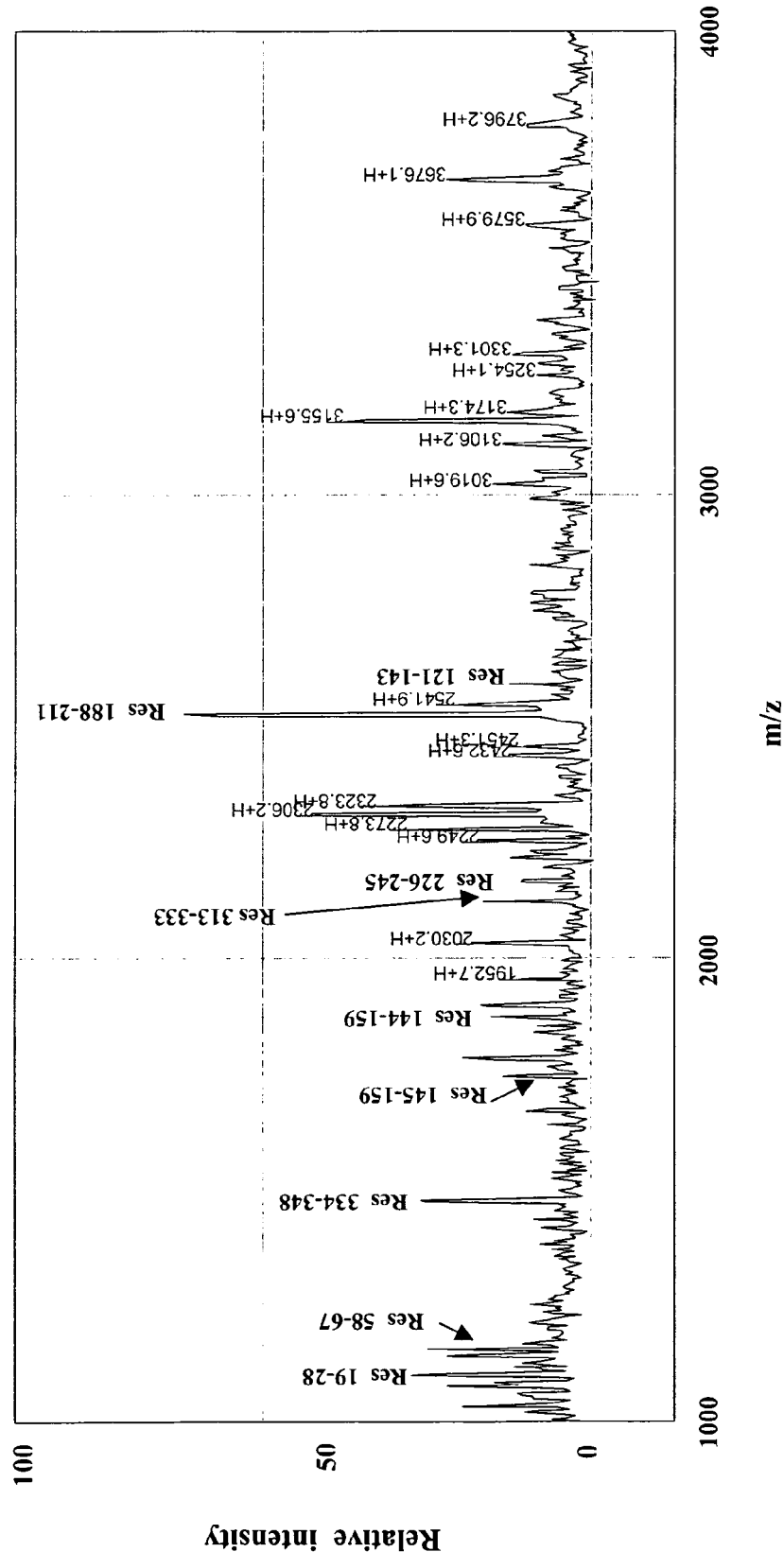
FIG. 6 shows a mass spectrum of 1 µg fetuin after its on-NP20 chip denaturation, reduction, alkylation, deglycosylation and trypsinization.

Fetuin was trypsinized (FIG. 6) following denaturation, reduction, alkylation and N-deglycosylation on NP20 chips. Its identity was confirmed with twelve peptides matched against the in-silico digest (Table 3). The MASCOT search through the SwissProt protein database showed that fetuin was ranked at the top of the list.

Figure 7:
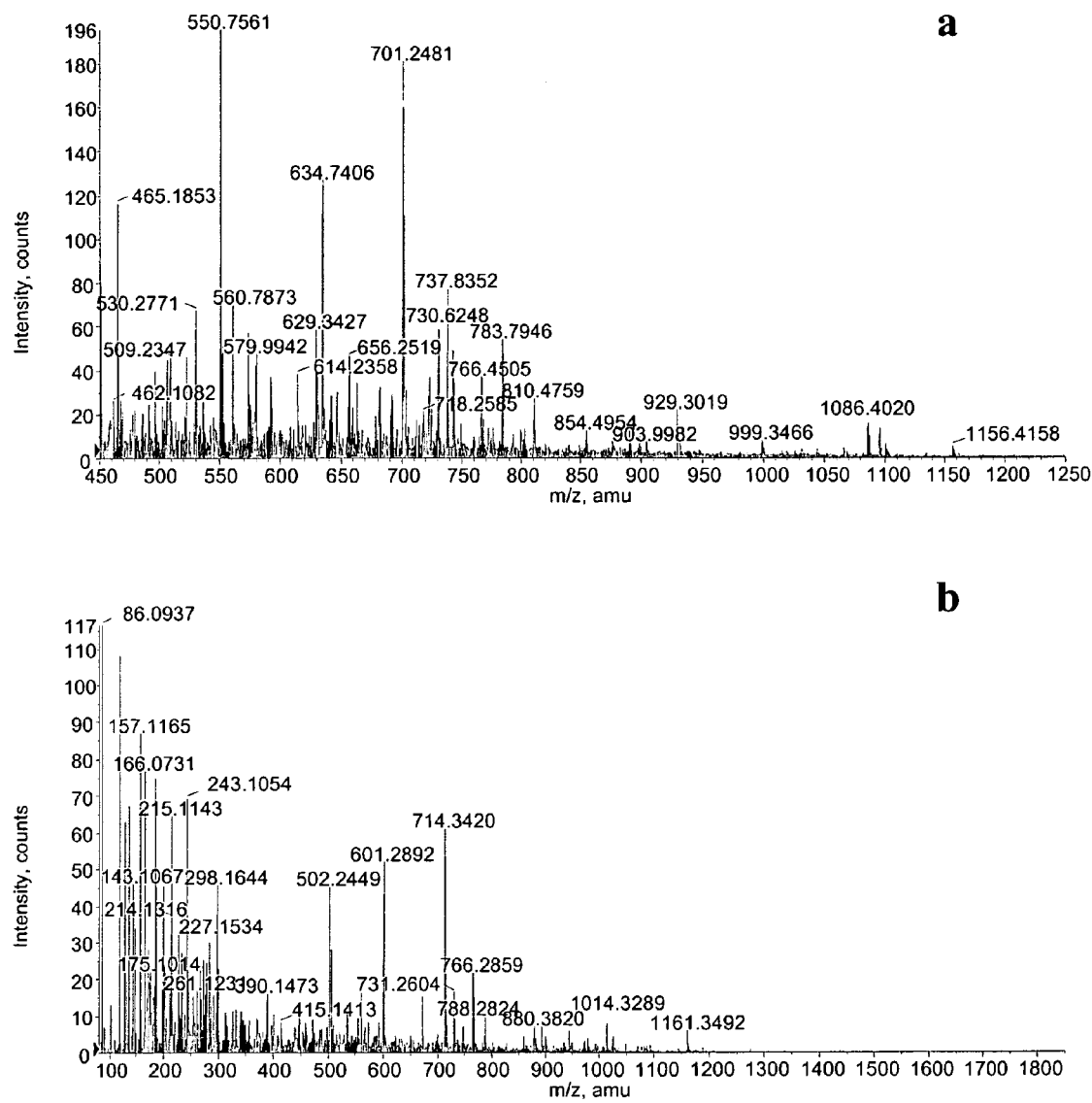
FIG. 7a shows the high resolution TOF mass spectrum of EGFRED reduced, alkylated, and trysinized on a H4 chip. The peptides were sequenced in product ion mode (FIG. 7b) and submitted to Mascot (Matrix Science Ltd. UK) for protein identification.
Figure 8:
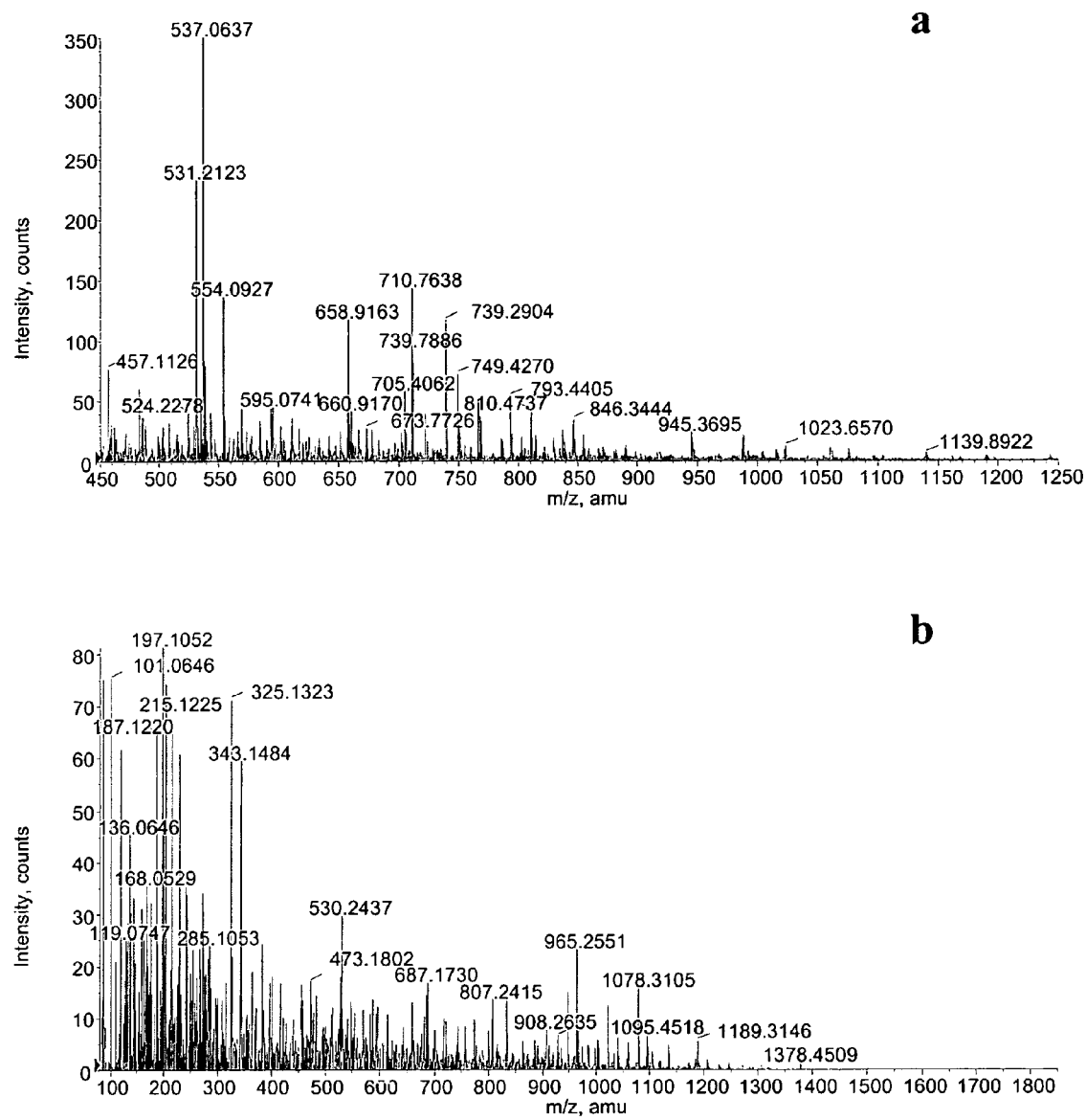
FIG. 8 shows the mass spectrum of ovalbumin after reduction, alkylation and digestion with the endoprotease Glu-C. The data was treated similar to FIG. 7 and the protein and impurities identified.
Figure 9:
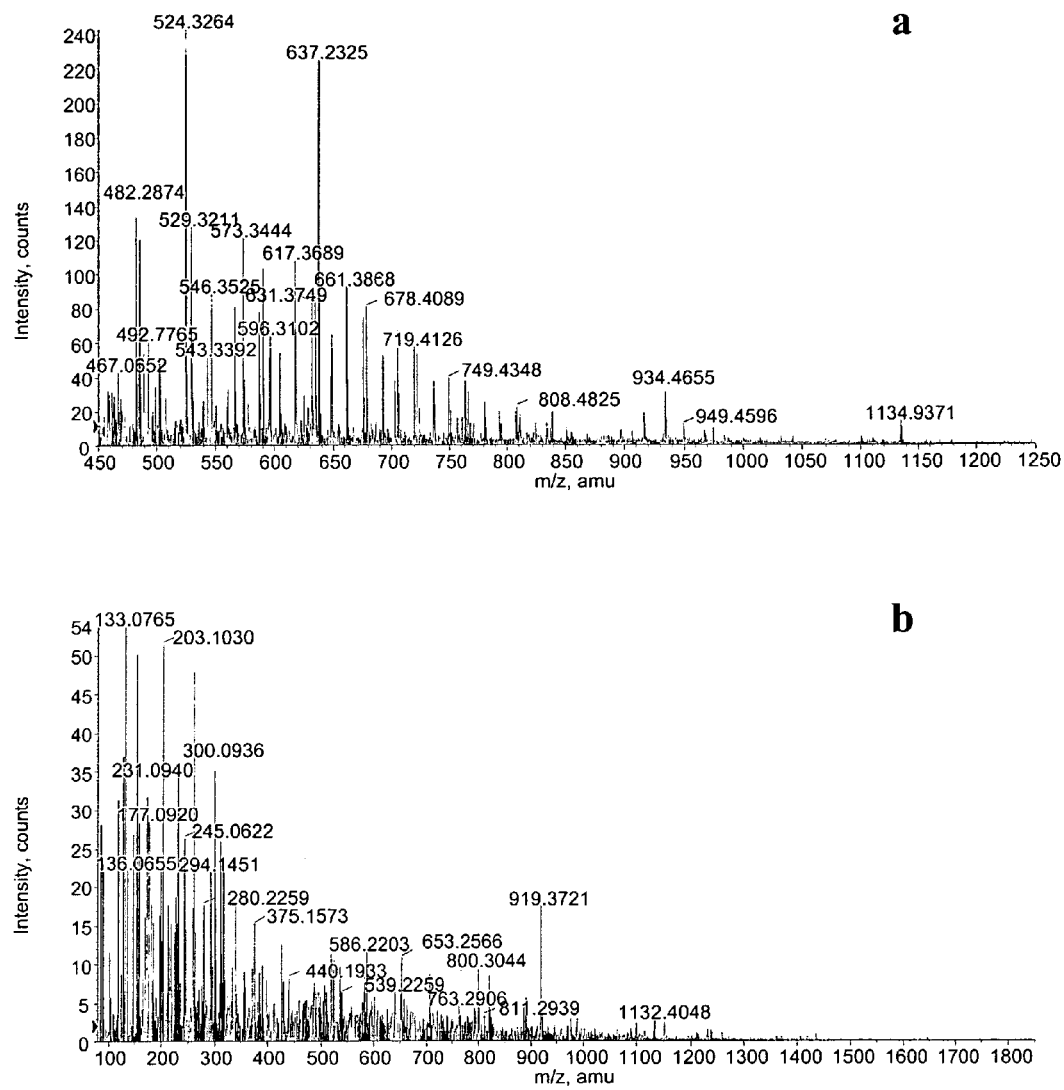
FIG. 9 shows fetuin after reduction, alkylation, deglycosation and chemically digested with formic acid. Data was treated as in FIGS. 7 and 8.

FIG. 7a shows the TOF mass spectrum of EGFRED reduced, alkylated, and trysinized on a H4 chip. The chip holder was connected to an ABI/Sciex QSTAR mass spectrometer. Several singly and multiple-charged peptides were obtained. The peptides were sequenced in product ion mode (FIG. 7b) and submitted to Mascot (Matrix Science Ltd. UK) for protein identification. In addition to numerous EGFRED peptides, contaminants from keratin, trypsin and other proteins were identified.

EXAMPLE 5

On-Chip Identification of Rat Urinary Proteins

Proteolysis of urinary proteins was also investigated by directly applying a urine aliquot on-chip and performing the reactions described. Ten μl of rat urine was applied, denatured, reduced, alkylated and trypsinized as described above. MS analysis and peptide mass fingerprinting identified 5 and 24 peptides specific to Alpha-2u-globulin (AUG) and rat urinary albumin (RUA) respectively. The sequence coverages of AUG and RUA are shown in Table 3. AUG is the most abundant in normal rat urine whereas RUA is most prevalent in puromycin-induced proteinuria. Both contain disulfide bridges and AUG is N-glycosylated. Their identities were independently confirmed by LCM S/MS[46,47].

TABLE 3

Proteins enzymatic treatment and identification

| Protein | Proteolytic enzyme | Number of proteolytic peptides | % Sequence coverage |
| --- | --- | --- | --- |
| EGFRED | Trypsin | 20 | 75.0 |
| | Arg-C | 15 | 51.4 |
| | Asp-N | 15 | 54.2 |
| | Glu-C | 17 | 57.1 |
| | Lys-C | 21 | 64.8 |
| | Pronase | 46 | 68.6 |
| Bovine fetuin | Trypsin | 12 | 59.8 |
| | Pronase | 36 | 73.7 |
| | Arg-C | 8 | 67.2 |
| Ovalbumin | Trypsin | 14 | 60.4 |
| | Asp-N | 12 | 73.8 |
| | Glu-C | 17 | 78.8 |
| Alpha-2u-globulin (AUG) | Trypsin | 5 | 59.3 |
| | Pronase | 28 | 65.4 |
| | Arg-C | 7 | 61.8 |
| Rat urinary albumin (RUA) | Trypsin | 24 | 55.7 |
| | Lys-C | 26 | 69.3 |
| | Glu-C | 23 | 76.8 |

In addition to the peptides derived from ovalbumin, EGFRED, fetuin and the rat urine proteins AUG and RUA, some ion peaks found in the protein digests were also present in the blank. Enzymatic autolysis and proteolysis products from N-glycosidase and human keratin were clearly identified.

On-chip chemical and enzymatic reactions are dependent on the physico-chemical properties of the chip surface. The interactions are analogous to those involved in normal and reverse phase chromatographic separations. For example, hydrophobic proteins will bind tighter to a reversed phase surface than hydrophilic proteins. These interactions determine the type of chip used for a particular on-chip experiment. As previously mentioned, the polarity of the binding buffer influences the selection of proteins that are retained on the chip.

Several chips are currently available for this protocol. These include anion and cation exchange, metal ion, antibody-antigen, receptor-ligand and DNA-protein interaction chips. Therefore the appropriate chip should be chosen for optimal reaction, selectivity and sensitivity. Complex samples (plasma, urine, cerebrospinal fluid etc.) may require fractionation or depletion strategies to isolate target proteins prior to the application of the methods of the present invention. Also, the present methods could provide a rapid means for characterizing native proteins or antibody therapeutics as well as chemically modified proteins and formulated protein products in the course of their manufacturing and quality control processes. Greater usefulness of this method can be attained if the chip is read by a high resolution (>12,000) mass spectrometer with high mass accuracy (<10 ppm). This will afford the microcharacterization of protein modifications. For example, single phosphorylation will show a monoisotopic difference of 79.9633 amu, the molecular weight of the phosphate moiety. Finally, as mentioned above, more than one chip could be chosen for a particular protein, proteins or sample, and the chips can be treated in parallel (with modifications of the treatment adapted for particular chips, if required and as known in the art) to optimize the method for best results.

CONCLUSION

Protein identification generally involves isolation of proteins of interest by electrophoresis and/or chromatographic methods followed by denaturation, reduction, alkylation and proteolytic (enzymatic or chemical) digestion. All steps are normally carried out in solution to generate peptides for Edman degradation or sequencing by MS methods. The major advantages of protocols of the present invention are their simplicity, speed and sensitivity. Low picomolar amounts of relatively complex proteins can be rapidly deglycosylated, dephosphorylated and/or proteolyzed and readily identified. The sequence coverages obtained by these methods are similar or even superior to that generated from in-solution digestion.

In conclusion, the herein-described approach to protein identification and characterization can be routinely used in several areas of biomarker research and related applications, particularly in molecular diagnostics and monitoring of disease, assessment of drug efficacy and basic proteomic research. The methods of the present invention work effectively for proteins which have complex structures as demonstrated by the analysis of EGFRED, fetuin, and ovalbumin. Thus, the on-chip deglycosylation and/or dephosphorylation and proteolysis of the present invention provide an excellent approach for rapid analysis of modified proteins.

Although the present invention has been described herein above by way of preferred embodiments thereof, it can be modified, without departing from the spirit and nature of the subject invention as defined in the appended claims.

REFERENCES

1. Aebersold, R.; Mann, M. Nature, 2003, 422, 198-207.
2. Fenn, J. B.; Mann, M; Meng, C. K.; Wong, S. F.; Whitehouse, C. M. Science, 1989, 246, 64-71

3. Tanaka, K. H.; Wake, H.; Ido, Y.; Akita, S.; Yoshida, Y.; Yoshida, I. Rapid Commun. Mass Spectrom., 1988, 8, 151-152
4. U.S. Pat. No. 5,719,060 "Method and Apparatus for Desorption and Ionization of Analytes," Hutchens and Yip, (1998)
5. U.S. Pat. No. 6,225,047 "Use of Retentate Chromatography to Generate Difference Maps," Hutchens and Yip, (2001)
6. Weinberger et al., "Time-of-flight mass spectrometry," in Encyclopedia of Analytical Chemistry, R. A. Meyers, ed., pp 11915-11918 John Wiley & Sons Chichesher (2000)
7. Petrocoin E. F., Ardekami A. m., Hitt, B. A., Levine, P. J. F., The Lancet 2002, 359, 572-577
8. Petrocoin E. F., Liotta L. A., Current Opinion in Biotechnology, 2004, 15,24-30
9. Petrocoin E. F., Liotta L. A., clinical chemistry, 2003, 49, 533-536.
10. Y. Ge, M. Aguiar, R. Masse, B. F. Gibbs, 18$^{th}$ Symposium of the Protein Society, San Diego, 2004
11. Gorg, A. In Advances in 2D gel techniques. Proteomics: A Trend Guide; Mann, M.; Blackstock, W. ed.; pp 3-6 Elsevier: London, (2000)
12. Link, A. J.; Eng, J.; Schieltz, D. M.; Carmack, E.; Mize, G. J.; Morris, D. R.; Garvik, B. M.; Yates, J. R. 3rd. Nat. Biotechnol., 1999, 17, 676-682.
13. Kierman, U. A.; Tubbs, K. A.; Nedelkov, D.; Niederkofler, E. E.; McConnell, E.; Nelson, R. W. J Proteome Res., 2003, 2, 191-197.
14. Merchant, M.; Weinberger, S. R. Electrophoresis, 2000, 21, 1164-1177.
15. Gevaert, K.; Vanderkerckhove, J. Electrophoresis. 2000, 21, 1145-1154.
16. Lin, S.; Tornatore, P.; King, D.; Orlando, R.; Weinberger, S. R. Proteomics, 2001, 1, 1172-1184.
17. Dare, T.; Davies, H. A.; Turton, J. A.; Lomas, L.; Williams, T. C.; York, M. J. Electrophoresis, 2002, 23, 3241-3251.
18. Caputo, E.; Moharram, R.; Martin, B. M. Anal. Biochem., 2003, 321, 116-124.
19. U.S. patent application 2005/0090016
20. Rudd, P. M.; Elliott, T.; Cresswell, P.; Wilson, I. A.; Dwek, R. A. Science, 2001, 291, 2370 -2376.
21. Kim, Y. J.; Varki, A. Glycoconj J, 1997, 14, 569-576
22. Zhen, Y.; Caprioli, R. M.; Staros, J. V. Biochemistry, 2003, 42, 5478-5492
23. Cohen, P. Nat. Rev. Drug Discovery, 2002 1, 309-315
24. Stein P. E.; Leslie A. G.; Finch J. T.; Turnell W. G.; McLaughlin P. J.; Carrell R. W. Nature, 1990, 347, 99-102
25. MacCoss M. J.; McDonald W. H.; Saraf, A.; Sadygov, R.; Clark, J. M.; Tasto, J. J.; Gould, K. L.; Wolters, D.; Washburn, M.; Weiss, A.; Clark, J. I.; Yates, J. R. 3rd. Proc. Natl. Acad. Sci. U.S.A. 2002, 99, 7900-7905
U.S. Pat. No. 5,118,937 "Process and device for the laser desorption of an analyte molecular ions, especially of biomolecules," Hillenkamp F, Karas M, Giessmann U (1992)
U.S. Pat. No. 5,045,694 "Instrument and method for the laser desorption of ions in mass spectrometry," Beavis R C, Chait B T (1991)
26. Y. Ge, M. Aguiar, R. Masse, B. F. Gibbs, 18$^{th}$ Symposium of the Protein Society, San Diego, 2004
27. Dictionary of Microbiology and Molecular Biology, 2nd ed. (Singleton et al., 1994, John Wiley & Sons, New York, N.Y.)
28. The Harper Collins Dictionary of Biology (Hale & Marham, 1991, Harper Perennial, New York, N.Y.)
29. Rieger et al., Glossary of genetics: Classical and molecular, 5th edition, Springer-Verlag, New-York, 1991
30. Alberts et al., Molecular Biology of the Cell, Garland science, New-York, 2002
31. Lewin, Genes VII, Oxford University Press, New-York, 2000
32. Sambrook et al. (2000, Molecular Cloning—A Laboratory Manual, Third Edition, Cold Spring Harbor Laboratories)
33. Ausubel et al. (1994, Current Protocols in Molecular Biology, John Wiley & Sons, New-York).
34. Laemmli, U.K. Nature (Lond.), 1970, 227, 680-685.
35. Practical protein chemistry, A handbook A. Darbre ed. Wiley John Wiley and sons. Copyright 1986.
36. Washburn, M. P.; Wolters, D.; Yates, J. R. Nat Biotechnol, 2001, 19, 242-247.
37. Yates, J. R. 3$^{rd}$ Annu Rev Biophys Biomol Struct, 2004, 33, 297-316.
38. Industrial proteomics Applications for Biotechnology and Pharmaceuticals. Daniel Figeys Ed. John wiley and Sons Copyright 2005.
39. Karas, M.; Hillenkamp, F. Anal. Chem., 1998, 60, 2299-2301.
40. Bradford, M. Anal. Biochem. 1976, 72, 248-254.
41. Duffin, K. L.; Welply, J. K.; Henion, J. D. Anal. Chem. 1992, 64, 1440-1448.
42. Spiro, R. G.; Bhoyroo, V. D. J. Biol. Chem. 1974, 249, 5704-5717.
43. Nilsson, B.; Norden, N. E.; Svensson, S. J. Biol. Chem. 1979, 254, 4545-4553.
44. Ge, Y.; Aguiar, M.; Masse, R.; Gibbs, B. F 52nd conference ASMS. May 2005, San Antonio, Tex.
45. Ge, Y.; Gibbs, B. F.; Masse, R. Anal. Chem., 2005, 77, 3644-3650.

What is claimed is:

1. A method for altering a posttranslationally modified protein or polypeptides directly bound to a protein chip, said method comprising subjecting said protein or polypeptide bound to said protein chip to at least two chemical and/or enzymatic reactions selected from the group consisting of:
   a) denaturation;
   b) reduction of disulfide bridges;
   c) alkylation;
   d) deglycosylation;
   e) dephosphorylation; and
   f) digestion of peptide bonds.

2. The method of claim 1, wherein at least 3 chemical and/or enzymatic reactions are performed.

3. The method of claim 1, wherein at least 4 chemical and/or enzymatic reactions are performed.

4. The method of claim 1, wherein at least 5 chemical and/or enzymatic reactions are performed.

5. The method of claim 1, wherein said protein chip has a surface which is
   a standard chromatography surface.

6. The method of claim 1, wherein said protein or polypeptide directly bound to said protein chip is selected from the group consisting of:
   a) enzymes;
   b) antibodies;
   c) ligands;
   d) receptors;
   e) DNA; and
   f) lectins.

7. The method of claim 1, wherein said digestion of peptide bonds is for mass fingerprinting or ms/ms ion search.

8. The method of claim 1, wherein said protein or polypeptide is comprised within a mixture.

9. The method of claim 8, wherein said mixture is selected from the group consisting of:
   a) a crude sample;
   b) a purified sample;
   c) a biological fluid sample.

10. The method of claim 1, wherein said digestion of peptide bonds is an enzymatic digestion.

11. The method of claim 1, wherein said digestion of peptide bonds is a chemical digestion.

12. The method of claim 1, wherein said altering is for mass spectrometry.

13. The method of claim 12, wherein a sequence coverage of at least 30% is reached.

14. The method of claim 12, wherein a sequence coverage of at least 60% is reached.

15. A method for altering a posttranslationally modified protein or polypeptide directly bound to a protein chip, said method comprising:
   a) loading a mixture containing said protein or polypeptide on said chip surface;
   b) denaturing said protein or polypeptide on said chip surface;
   c) reducing said protein or polypeptide on said chip surface;
   d) performing at least one of the following:
      i) deglycosylating said protein or polypeptide on said chip surface;
      ii) dephosphorylating said protein or polypeptide on said chip surface;

iii) chemically and/or enzymatically cleaving said protein or polypeptide on said chip surface; and iv) digesting said protein or polypeptide on said chip surface; and e) performing mass spectrometry on said chip.

16. The method of claim 15, wherein said digesting is enzymatic.

17. The method of claim 15, wherein said digesting is chemical.

18. The method of claim 15, wherein said mixture is selected from the group consisting of:

(a) a purified sample;

(b) a crude sample; and (c) a biological sample.

19. The method of claim 15, further comprising a washing step prior to mass spectrometry for removal of interfering molecules.

* * * * *